US010195378B2

United States Patent
Truschel et al.

(10) Patent No.: US 10,195,378 B2
(45) Date of Patent: Feb. 5, 2019

(54) POWER CONTROL IN A MEDICAL VENTILATOR

(71) Applicant: KONINKLIJKE PHILIPS N.V., Eindhoven (NL)

(72) Inventors: William A. Truschel, Oakmont, PA (US); Ljubisa Milojevic, Pittsburgh, PA (US); Ronald Cyprowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 571 days.

(21) Appl. No.: 14/817,251

(22) Filed: Aug. 4, 2015

(65) Prior Publication Data

US 2015/0335838 A1    Nov. 26, 2015

Related U.S. Application Data

(63) Continuation of application No. 13/124,132, filed as application No. PCT/IB2009/054453 on Oct. 9, 2009.
(Continued)

(51) Int. Cl.
*A61M 16/00* (2006.01)
*A61M 16/12* (2006.01)
(Continued)

(52) U.S. Cl.
CPC ........ *A61M 16/0003* (2014.02); *A61M 16/00* (2013.01); *A61M 16/0051* (2013.01);
(Continued)

(58) Field of Classification Search
CPC .............. A61M 16/00; A61M 16/0051; A61M 2205/33; A61M 2205/82;
(Continued)

(56) References Cited

U.S. PATENT DOCUMENTS

| 4,297,590 A | 10/1981 | Vail |
| 5,148,802 A | 9/1992 | Sanders |

(Continued)

FOREIGN PATENT DOCUMENTS

| CN | 1832295 A | 9/2006 |
| EP | 1858233 A1 | 11/2007 |
| WO | WO0049722 A1 | 8/2000 |

*Primary Examiner* — Michael Tsai
(74) *Attorney, Agent, or Firm* — Michael W. Haas

(57) ABSTRACT

A ventilator that is small, lightweight, and portable, yet capable of being quickly adapted to operate in a plurality of different modes and configurations to deliver a variety of therapies to a patent. A porting system having a plurality of sensors structured to monitor a number of parameters with respect to the flow of gas, and a number of porting blocks is used to reconfigure the ventilator so that it operates as a single-limb or dual limb ventilator. In the single-limb configuration, an active or passive exhaust assembly can be provided proximate to the patient. The ventilator is capable of operate in a volume or pressure support mode, even in a single-limb configuration. In addition, a power control mechanism controls the supply of power to the ventilator from an AC power source, a lead acid battery, an internal rechargeable battery pack, and a detachable battery pack.

19 Claims, 14 Drawing Sheets

Related U.S. Application Data

(60) Provisional application No. 61/106,330, filed on Oct. 17, 2008.

(51) Int. Cl.
*A61M 16/20* (2006.01)
*A61M 16/08* (2006.01)
*A61M 16/10* (2006.01)

(52) U.S. Cl.
CPC .... *A61M 16/0057* (2013.01); *A61M 16/0069* (2014.02); *A61M 16/0841* (2014.02); *A61M 16/125* (2014.02); *A61M 16/202* (2014.02); *A61M 16/205* (2014.02); A61M 16/0066 (2013.01); *A61M 16/0816* (2013.01); *A61M 16/107* (2014.02); A61M 2016/0027 (2013.01); A61M 2016/0036 (2013.01); A61M 2016/0039 (2013.01); A61M 2205/125 (2013.01); A61M 2205/17 (2013.01); A61M 2205/18 (2013.01); A61M 2205/3368 (2013.01); A61M 2205/35 (2013.01); A61M 2205/505 (2013.01); A61M 2205/583 (2013.01); A61M 2205/6045 (2013.01); A61M 2205/8206 (2013.01); A61M 2205/8237 (2013.01); A61M 2205/8262 (2013.01)

(58) Field of Classification Search
CPC .. A61M 2205/8206; A61M 2205/8212; A61M 2205/8237; A61M 2205/8256; A61M 2205/8262; H02J 9/00; H02J 9/04; H02J 9/06; H02J 9/061; H02J 2007/0067; H02J 7/0063; H02J 7/0024; H02J 7/0068
See application file for complete search history.

(56) References Cited

U.S. PATENT DOCUMENTS

| | | | | |
|---|---|---|---|---|
| 5,212,021 | A * | 5/1993 | Smith | H01M 2/1022 348/E5.025 |
| 5,313,937 | A | 5/1994 | Zdrojkowski | |
| 5,433,193 | A | 7/1995 | Sanders | |
| 5,632,269 | A | 5/1997 | Zdrojkowski | |
| 5,741,305 | A * | 4/1998 | Vincent | A61N 1/39 439/500 |
| 5,803,065 | A | 9/1998 | Zdrojkowski | |
| 5,931,159 | A | 8/1999 | Suzuki | |
| 6,029,664 | A | 2/2000 | Zdrojkowski | |
| 6,232,674 | B1 | 5/2001 | Frey | |
| 6,360,741 | B2 | 3/2002 | Truschel | |
| 6,373,226 | B1 | 4/2002 | Itou | |
| 6,626,175 | B2 | 9/2003 | Jafari | |
| 6,661,649 | B2 | 12/2003 | Tanaka | |
| 6,920,875 | B1 | 7/2005 | Hill | |
| 6,948,497 | B2 | 9/2005 | Zdrojkowski | |
| 7,040,318 | B2 | 5/2006 | Dascher | |
| 7,100,607 | B2 | 9/2006 | Zdrojkowski | |
| 7,188,621 | B2 | 3/2007 | Devries | |
| 7,252,088 | B1 | 8/2007 | Nievez-Ramirez | |
| 2004/0035424 | A1 | 2/2004 | Wiesmann | |
| 2004/0189248 | A1 | 9/2004 | Boskovitch | |
| 2006/0103242 | A1 | 5/2006 | Lin | |
| 2006/0287013 | A1 | 12/2006 | Kim | |
| 2008/0136778 | A1 | 6/2008 | Hursh | |
| 2008/0254349 | A1* | 10/2008 | Gong | H04M 1/0262 429/96 |
| 2010/0084999 | A1 | 4/2010 | Atkinson | |

* cited by examiner

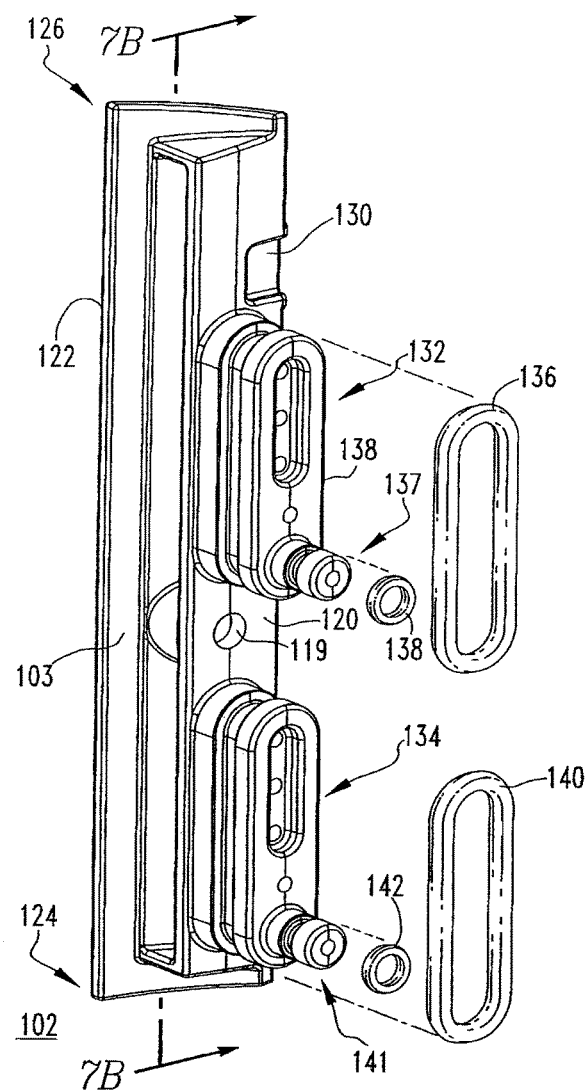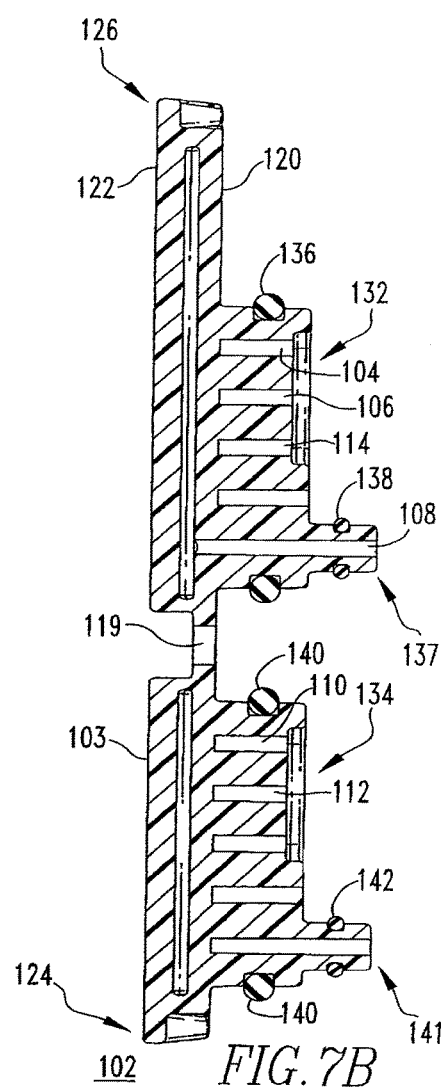
FIG. 7A
FIG. 7B

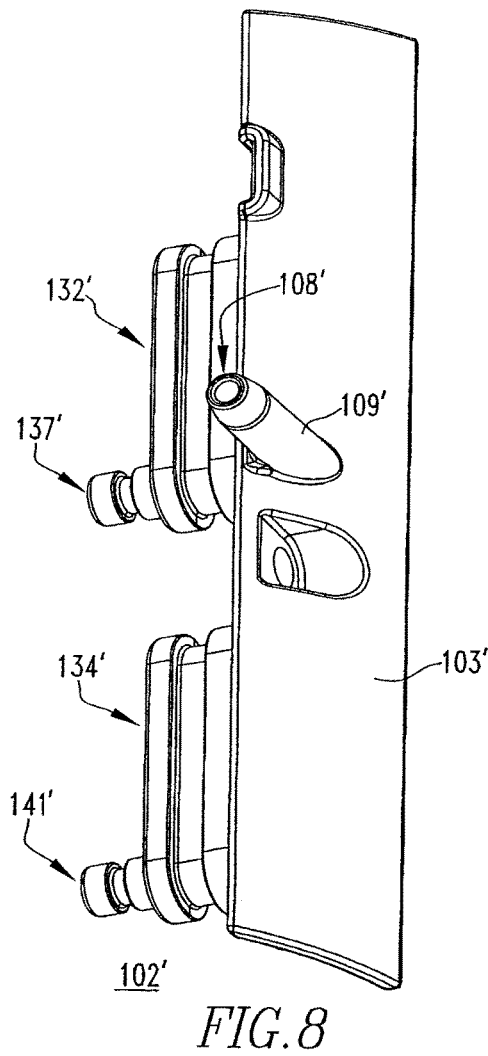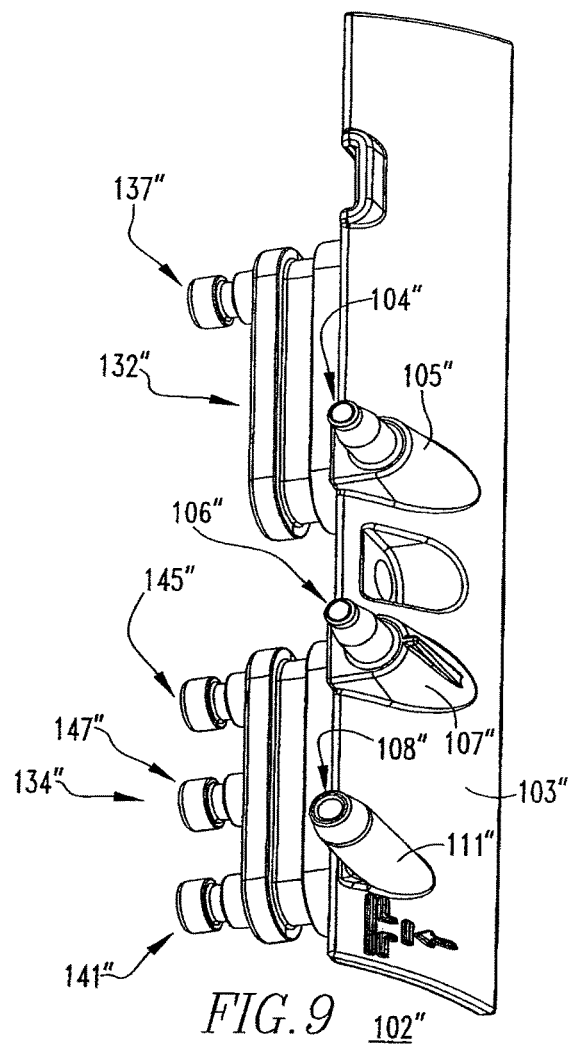

POWER CONTROL IN A MEDICAL VENTILATOR

This patent application claims the priority benefit under 35 U.S.C. § 119(e) of U.S. Provisional Application No. 61/106,330 filed on Oct. 17, 2008, the contents of which are herein incorporated by reference.

The invention relates generally to medical ventilators and, more particularly, to a medical ventilator that is relatively small, lightweight, and portable, yet is capable of being quickly and easily adapted to operate in a plurality of different modes and configurations to deliver a variety of ventilation therapies to a patent. The invention also relates to methods of operating and servicing such a ventilator.

A medical ventilator is a machine that is structured to deliver a gas, such as air, oxygen, or a combination thereof, to an airway of patient to augment or substitute the patient's own respiratory effort. It is generally known to operate a conventional medical ventilator in a particular mode depending upon the specific ventilation therapy needs of the patient.

In a life support situation, where there is substantially no spontaneous respiratory effort by the patient, a controlled mode of ventilation is typically provided, where the ventilator assumes full responsibility for ventilating the patient. In this mode of ventilation, a controlled volume of gas is delivered to the patient during each inspiratory phase of the ventilatory cycle, and the trigger point (i.e., the transition from the expiratory phase to the inspiratory phase of the ventilatory cycle) and cycle point (i.e., the transition from the inspiratory phase to the expiratory phase of the ventilatory cycle) of the ventilator are typically determined based on time.

Traditionally, ventilators used in life support situations employ what is known as a dual-limb patient circuit, which has an inspiratory limb for carrying gas to the patient, and an expiratory limb for carrying gas from the patient to an exhaust assembly. The exhaust assembly includes a selectively controllable valve or similar mechanism for actively controlling the discharge of the gas that has been expired from the patient during the expiratory phase of the ventilatory cycle to the atmosphere. Such a configuration is commonly referred to as an "active exhaust" or "active exhalation" configuration. Typically, the aforementioned controlled volume life support ventilation is invasive, meaning that the patient interface (e.g., without limitation, tracheostomy tube, endotracheal tube, etc.) which is employed to interface the patient circuit to the airway of the user, is inserted directly into the patient's airway and is structured to remain there for an extended period of time.

In non-life support situations, where the patient exhibits some degree of spontaneous respiratory effort, an assist mode or a support mode of ventilation is typically provided in which the ventilator augments or assists in the patient's own respiratory efforts, typically by providing a predetermined pressure to the airway of the patient. In this mode of ventilation, the pressure of the flow of gas is controlled. For example, in bi-level non-invasive ventilation, an inspiratory positive airway pressure (IPAP) is delivered to the patient during the inspiratory phase of each ventilatory cycle, and an expiratory positive airway pressure (EPAP), which is typically lower than the IPAP level, is delivered to the patient during the expiratory phase of each ventilatory cycle.

Some ventilators that are adapted for used in non-life support situations employ what is known as a single-limb patient circuit; having only one limb that is used for carrying gas both to and from the patient. Traditionally, such single-limb circuits employ a passive exhalation device, often in the form of a hole or exhaust port in the limb and/or the patient interface, to allow the patient's expired gas to be passively vented to the atmosphere. Such a configuration is commonly referred to as a "passive exhaust" or "passive exhalation" configuration.

Additionally, unlike the aforementioned invasive patient interface(s) that are commonly associated with volume control ventilation, the patient circuit for pressure support ventilation therapy is typically non-invasive. For example and without limitation, a nasal mask, nasal oral mask, full face mask, or a nasal canula, is temporarily employed by the patient to receive the pressurized gas from the ventilator on an as-needed basis.

In view of the foregoing, it will be appreciated that the ventilators and associated ventilator hardware, and the associated methods of employing the same to administer ventilation therapy to the patient, have traditionally been significantly different for volume control ventilation operating modes than for pressure support operating modes. Moreover, known ventilators, ventilator hardware and/or associated methods for one of these two modes (e.g., pressure support) are often not compatible with ventilators, ventilator hardware and/or associated methods for the other modes (e.g., volume control).

Accordingly, it is an object of the present invention to provide a ventilator that overcomes the shortcomings of conventional ventilator. This object is achieved according to one embodiment of the present invention by providing a ventilator that including a housing, an inlet port, a flow generator structured to generate a flow of gas, and an outlet port structured to discharge the flow of gas from the housing. The ventilator is capable of being operable among a plurality of different modes. In addition, the ventilator includes a porting system having a plurality of sensors structured to monitor a number of parameters with respect to the flow of gas, and a number of porting blocks. Each blocking port includes a removable routing element structured to be selectively coupled to the housing of the ventilator in order to configure the sensors in one of a plurality of different predetermined configurations corresponding to a desired one of the modes of operation of the ventilator. A fastening mechanism fastens the removable routing element to the housing of the ventilator.

In a further embodiment, this object is achieved by providing a ventilator that includes a housing having an interior and an exterior, an inlet port extending from the exterior to the interior of the housing, a flow generator disposed within the housing and that generates a flow of gas, a outlet port adapted to discharge the flow of gas from the housing. A patient circuit including a patient interface and a passive exhalation device is in fluid communication with the outlet port to deliver the flow of gas to an airway of a patient. A controller is disposed in the housing and being operatively coupled to the flow generator. The controller controls an inhalation volume of the flow of gas, wherein when the patient exhales an exhalation gas during an expiratory phase of the ventilatory cycle, the passive exhalation device discharges at least a portion of the exhalation gas to the atmosphere.

In a still further embodiment, this object is achieved by providing a ventilator that includes a housing having an interior and an exterior, an inlet port extending from the exterior to the interior of the housing, a flow generator disposed within the housing that generates a flow of gas, and an outlet port adapted to discharge the flow of gas from the housing to an airway of a patient during an inspiratory phase of a ventilatory cycle. A controller disposed in the housing operate the ventilator among a plurality of different modes, wherein the modes include a first mode for providing pressure support ventilation therapy to the patient and a second mode for providing volume control ventilation therapy to the patient.

In yet another embodiment, this object is achieved by providing a ventilator that includes a housing having an interior and an exterior, an inlet port extending from the exterior to the interior of the housing, a flow generator disposed within the ventilator that generates a flow of gas, and an outlet port for discharging the flow of gas from the housing. The ventilator also includes an inlet airflow assembly having a cover member selectively coupled to the housing of the ventilator at or about the inlet port. The cover member has a first side, a second side disposed opposite the first side, and an inlet aperture extending through the cover member. The inlet aperture delivering a gas to the inlet port of the ventilator. A number of filtering members are disposed between the first side of the cover member and the housing of the ventilator. In addition, a fastening mechanism attaches the cover member to the housing of the ventilator, thereby securing the cover member and the number of filtering members with respect to the housing. The inlet airflow assembly is removable from the housing, without requiring the remainder of the ventilator to be disassembled.

In another embodiment, this object is achieved by providing a ventilator having a housing providing a first power connection being electrically connectable to an alternating current (AC) power source. The ventilator includes a second power connection being electrically connectable to a lead acid battery. An internal rechargeable battery pack is also disposed within the interior of the housing. Finally, a detachable battery pack is removably coupled to the exterior of the housing. A power control mechanism controls the supply of power to the ventilator from a corresponding at least one of the AC power source, the lead acid battery, the internal rechargeable battery pack, and the detachable battery pack.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIGS. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

FIG. 7A is an perspective view of the porting block of the porting system of FIG. 3;

FIG. 7B is a sectional view take along line 7B-7B of FIG. 7A;

FIG. 8 is an perspective view of another porting block for the porting system of the medical ventilator;

FIG. 9 is an isometric view of another porting block for the porting system of the medical ventilator;

Figure 1:
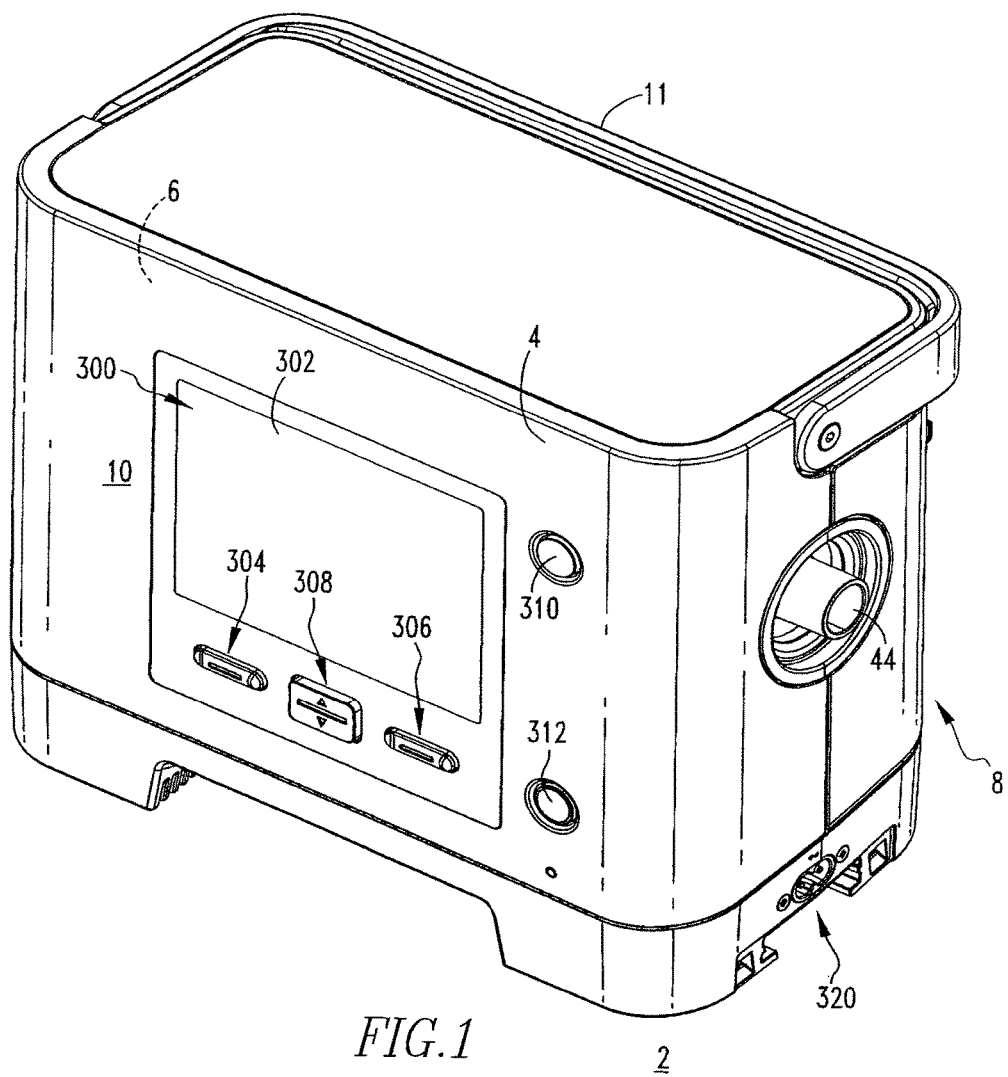
FIG. 1 is front perspective view a medical ventilator in accordance with an embodiment of the invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "patient interface" refers to any known or suitable mechanism for establishing fluid communication between the ventilator and an airway of a patient and expressly includes, but is not limited to, non-invasive patient interfaces, such as masks, nasal canulas, combination nasal/oral masks, and removable mouth pieces, and invasive patient interfaces, such as tracheal tubes and endotracheal tubes, as well as humidifiers, nebulizers and meter dose inhalers, which can be invasive or non-invasive.

As employed herein, the term "mode" refers to the manner in which the ventilator is operated in order to provide a particular type of ventilation therapy, (e.g., without limitation, pressure support ventilation therapy; volume control ventilation therapy) to the patient.

As employed herein, the term "probe" refers to any known or suitable sensing element (e.g., without limitation, a conduit), which is in communication with a sensor (e.g., without limitation, a machine flow sensor; a proximal pressure sensor; a monitor flow sensor), and is structured to relay information concerning a parameter (e.g., without limitation, pressure) to the sensor.

As employed herein, the term "interface mechanism" refers to any known or suitable device (e.g., without limitation, connector, receptacle, or plug) for connecting the ventilator to an accessory (e.g., without limitation, an oxygen blender, a humidifier, a pulse oximeter), device (e.g., without limitation, a printer), or communication or memory device (e.g., without limitation, the Internet; a hard drive disk, CD or other suitable storage medium; a computer).

As employed herein, the terms "fastener" and "fastening mechanism" refer to any known or suitable securing mechanism(s) for securing one part to another part, and expressly include, but are not limited to, rivets, screws, bolts, combinations of bolts, washers and/or nuts, as well as integral securing mechanisms such as, for example and without limitation, molded tabs and resilient protrusions, which extend from one part and engage another part to secure the parts together.

As employed herein, the statement that two or more parts are "coupled" together shall mean that the parts are joined together either directly or joined through one or more intermediate parts.

As employed herein, the term "number" shall mean one or an integer greater than one (i.e., a plurality).

A. System Architecture

FIG. 1 shows an illustrative embodiment of a medical ventilator 2 in accordance with an embodiment of the invention. As will be described in greater detail hereinbelow, medical ventilator 2 (sometimes referred to herein simply as "the ventilator") is capable of being selectively configured operate in a plurality of different modes, as defined herein, to provide ventilation therapy to a patient 170 (partially shown in simplified form in FIGS. 4, 5, and 6). It should be understood that ventilator 2 is shown and described herein for illustrative purposes only, and that the features and methods described herein may be implemented in other types of ventilators (not shown) having various other capabilities and modes of operation.

Ventilator 2 includes a housing 4 having an interior 6, and an exterior 8 with an exterior surface 10. In an exemplary embodiment, ventilator 2 is designed to be portable and, therefore, includes a handle 11, which is pivotably coupled to the top of the housing, in order to facilitate carrying or moving of the ventilator. Handle 11, which is shown in the stowed position in FIG. 1, is also shown in the upright position in phantom line drawing in FIG. 3.

Figure 4:
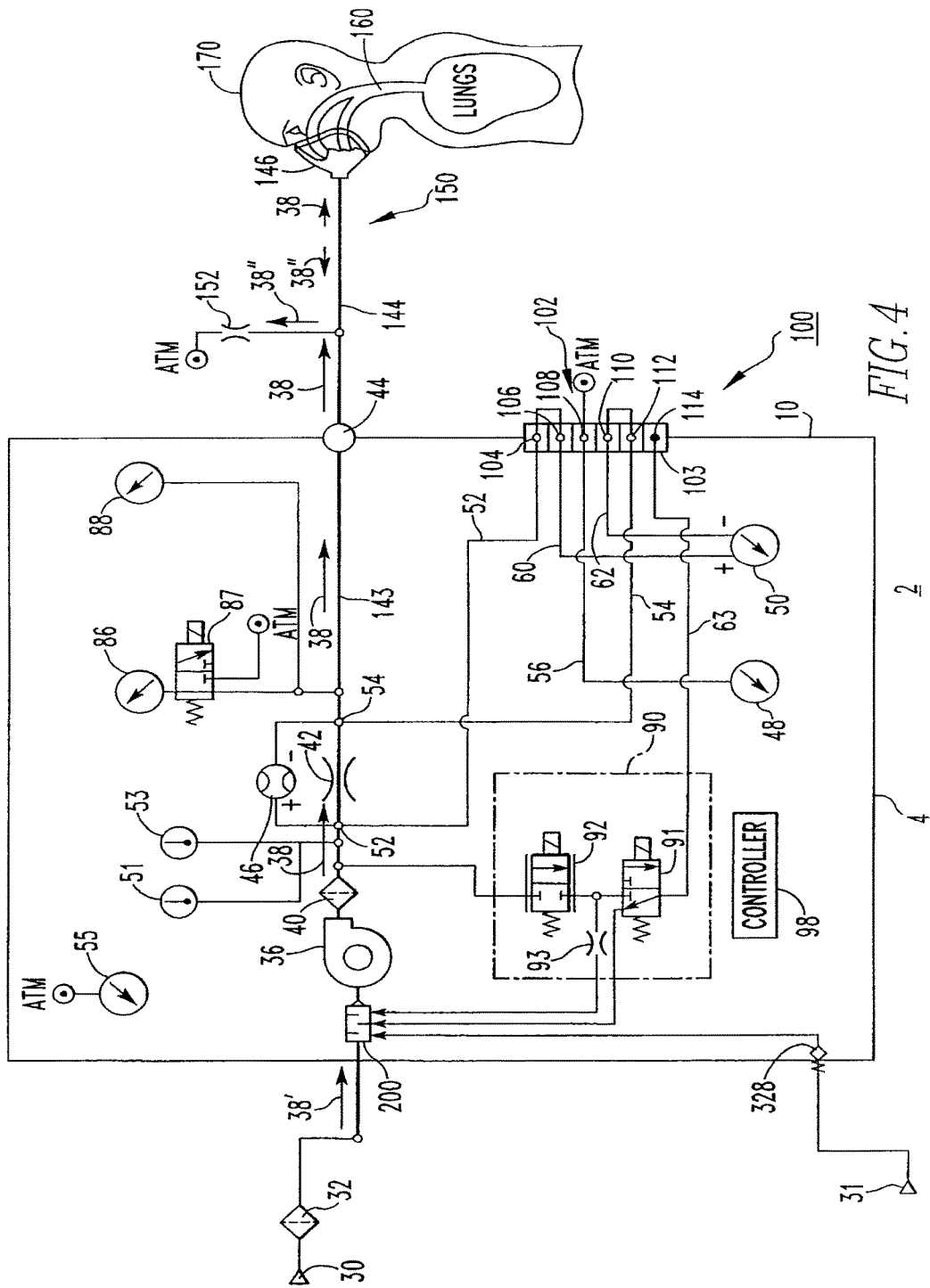
FIG. 4 is a schematic view of a medical ventilator and components therefor arranged in a passive exhalation without proximal pressure sensing configuration.
Figure 5:
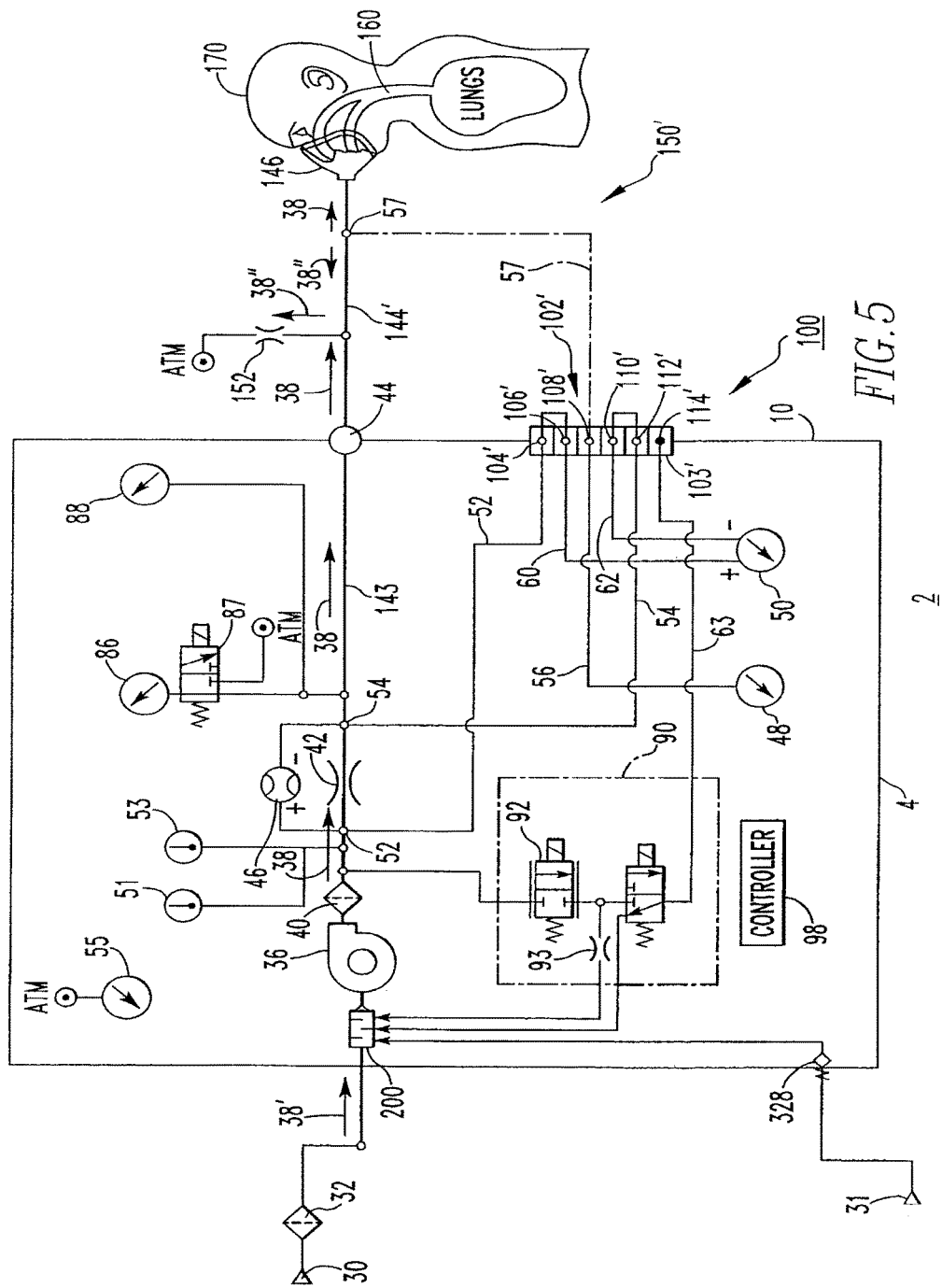
FIG. 5 is a schematic view of the medical ventilator of FIG. 4, modified to show the medical ventilator and components therefor arranged in a passive exhalation with a proximal pressure sensing configuration.
Figure 6:
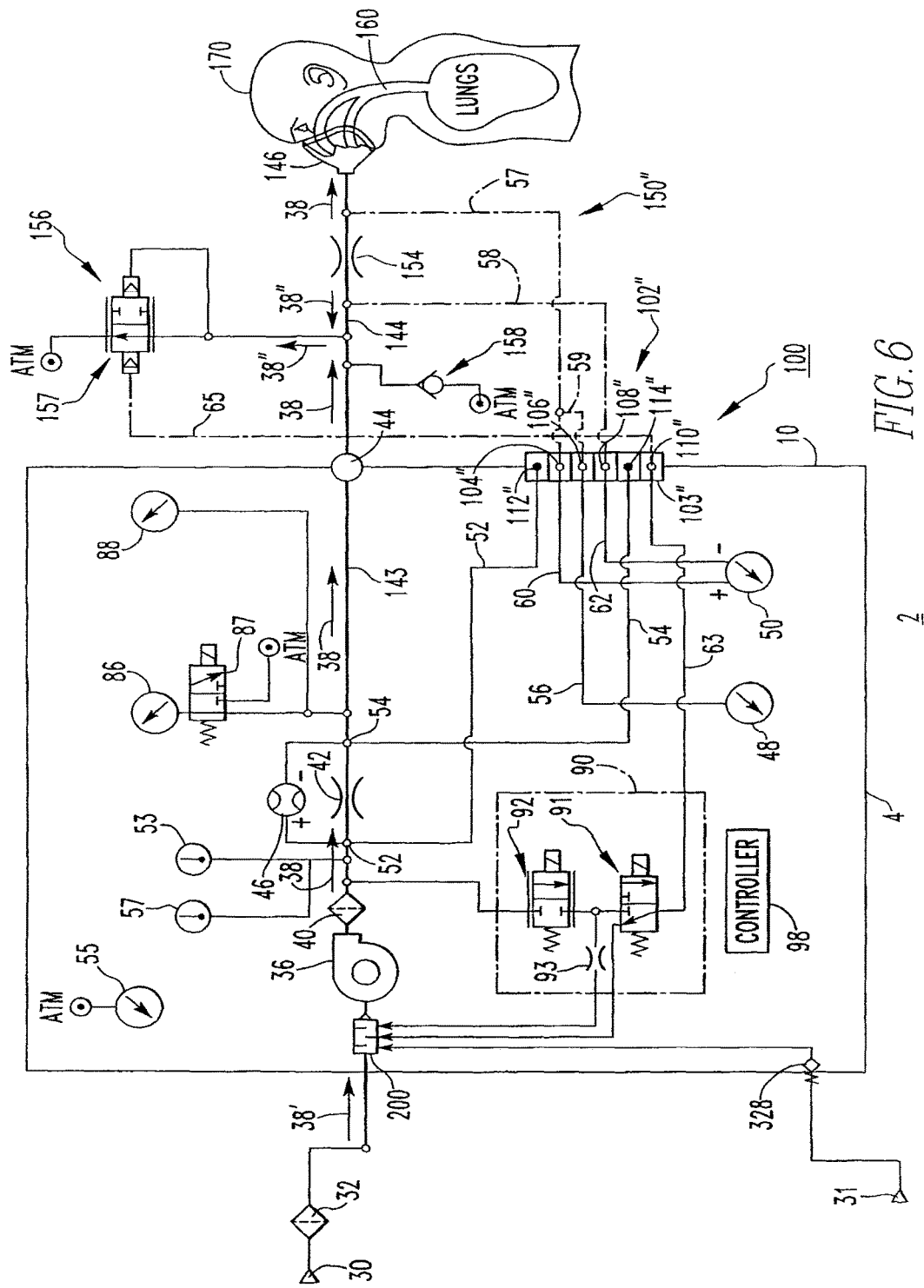
FIG. 6 is a schematic view of the medical ventilator of FIG. 5, modified to show the medical ventilator and components therefor arranged in an active exhalation configuration.

In the example of FIG. 1, ventilator 2 includes a user interface 300, which is disposed on exterior surface 10 at the front of ventilator housing 4. Among other features, user interface 300 includes a screen or display 302, which is structured to display a number of parameters (e.g., without limitation, pressure, volume, flow rate) relating to the ventilator and/or the patient 170 (FIGS. 4, 5 and 6). User interface 300 also includes a plurality of input members 304, 306, 308, 310, and 312, which are manipulatable by the user, for example, in order to control the operation of the ventilator and/or to navigate among the parameters (not expressly shown) displayed on screen 302. For example and without limitation, in one non-limiting example embodiment, input member 310 comprises an ON/OFF button and input member 312 comprises a mode button for switching among the various modes of operation of ventilator 2, or among various displays viewable on screen 302 of user interface 300. Similarly, input members 304, 306, and 308 could, for example and without limitation, comprise buttons employable by the user to navigate, select and/or program various features of the ventilator via the user interface.

It will, however, be appreciated that the particular arrangement of the user interface 300 is not meant to be a limiting aspect of the present invention. Specifically, it will be understood that the ventilator 2 could have any known or suitable alternative user interface with any suitable configuration other than that which is shown and described herein. For example, the present invention contemplated providing dials, knows, touch pads, roller balls, a mouse, or other input device, in addition to or in place of input members 304, 306, 308, 310, and 312. Also, display 203 can be configured as a touch screen display so that it functions as an input device, in addition to or in place of input members 304, 306, 308, 310, and 312. Also, the present invention contemplates operating ventilator 2 via a remote control, so that the input members 304, 306, 308, 310, and 312 can be eliminated.

Ventilator 2 also preferably has a variety of different interface mechanisms 320, 322, 324, 326, 328, and 330 as defined herein. For example and without limitation, ventilator 2 may include a receptacle 320, such as the one disposed toward the bottom of ventilator housing 4 in the example shown in FIG. 1. In one non-limiting embodiment of the invention, such receptacle 320 could be adapted to electronically connect ventilator 2 to a power source (see, for example, alternating current (AC) power source 402 and lead acid battery power source 406, schematically shown in FIG. 12 and described in greater detail hereinbelow). Any known or suitable type, number, and/or configuration of interface mechanisms such as, for example and without limitation, the five additional interface mechanisms 322, 324, 326, 328, and 330 shown in FIGS. 2 and 3, can be provided within the scope of the invention.

It will also be appreciated that such interface mechanisms (e.g., without limitation, receptacles; connectors) can be employed for any known or suitable purpose such as, for example and without limitation, to connect ventilator 2 to the Internet (by, for example, an Ethernet network), to a separate device such as, for example and without limitation, a printer (not shown) or computer (not shown), or to any suitable ventilator accessory such as an accessory medical device like a pulse oximeter or a carbon dioxide monitor, or an alternative gas source (see, for example, optional oxygen source 31, schematically shown in FIGS. 4, 5 and 6 and described hereinbelow).

FIGS. 4, 5 and 6, respectively, show three illustrative example configurations of ventilator 2, in simplified form. Specifically, FIG. 4 shows the components of the ventilator configured to provide passive exhalation without proximal pressure sensing. FIG. 5 shows the components of the ventilator configured for providing passive exhalation with proximal pressure sensing. In addition, FIG. 6 shows the components of the ventilator configured to provide active exhalation.

More specifically, as schematically shown in FIG. 4, ventilator 2 includes a flow generator 36, which is structured to generate a flow of gas 38, for example, from air 38' (ambient atmosphere) that enters the ventilator housing 4 through an inlet port 30 and/or a mixture of air 38' with a suitable supplemental gas, such as oxygen. The supplemental oxygen can be provided from one of the aforementioned ventilator accessories, such as an oxygen source 31, shown in simplified form in FIGS. 4, 5 and 6. In one non-limiting embodiment of the invention, oxygen source 31, which is optional, comprises a low-flow (e.g., without limitation about 0-50 psi and about 15 liters per minute (LPM) oxygen blender, which is connected to ventilator 2 via one of the aforementioned interface mechanisms such as, for example and without limitation, interface mechanism 328, which in the example schematically shown and described herein is a quick-connect valve fitting.

In the illustrated exemplary embodiment, ventilator 2 also includes an air inlet filter 32 for filtering ambient air 38' entering ventilator housing 4. As will be discussed in greater detail hereinbelow, ambient air 38' and/or the gas from the optional supplemental oxygen source 31 is preferably directed through an inlet airflow assembly 200, prior to reaching the flow generator 36. The example flow generator 36 is a micro-turbine comprising a blower assembly having a brushless direct current (DC) motor (not shown) with an impeller design (partially shown in FIG. 11) for generating the desired pressures and flows of gas 38, which are required by ventilator 2. In one non-limiting embodiment, the micro-turbine 36 is operable at a speed of about 3,000-42,000 revolutions per minute (rpm). It will, however, be appreciated that flow generator 36 could be any known or suitable device structured to create the flow of gas 38 at a pressure greater than ambient atmosphere such as, for example and without limitation, a compressor, a fan, an impeller, a blower, a piston, or bellows.

Continuing to refer to FIG. 4, the flow of gas 38 exiting flow generator 36 passes through an optional flow screen (filter) 40, which is in fluid communication with a first flow element 42 disposed in housing 4. Because first flow element 42 is disposed within the ventilator, it is also referred to herein as machine flow element 42. Machine flow element 42, which is positioned proximate the outlet of flow generator 36 may, for example and without limitation, be a mechanical element, such as an orifice or valve. Machine flow element 42 is designed to produce a pressure drop when the flow of gas 38 passes through it. It will be understood, however, that any known or suitable alternative number and/or configuration of flow elements could be employed to provide any suitable flow of gas 38 for ventilator 2, without departing from the scope of the invention.

A first (machine) flow sensor 46 is provided in tandem with machine flow element 42, in order to measure the flow rate of gas flow 38 based on the pressure drop across the machine flow element. In addition, a second flow sensor 50, which in the example shown and described herein is a differential pressure sensor, is also provided to measure the flow rate of gas 38 by measuring the pressure drop across machine flow element 42 via lines 52 and 54. Second flow sensor 50 thus monitors the volumetric flow of gas 38 in a redundant manner with that done by first flow sensor 46. Second flow sensor 50 is also referred to herein as monitor flow sensor 50. It will be appreciated that flow sensors 46 and 50, and other sensors within the ventilator 2 are configurable and reconfigurable to a plurality of different configurations corresponding to the various operating modes of the ventilator, as will be described hereinbelow with respect to the examples of FIGS. 5 and 6. It can be further appreciated that only the ventilator need not have both flow sensors. In addition, the present invention even further contemplates eliminating one or both flow sensors in favor of measuring the flow rate, or a parameter indicative of the flow rate, using other techniques, such as based on the power provided to flow generator, the speed of the flow generator, etc.

A control machine pressure sensor 86 is operatively coupled to an internal conduit 143 that supplies the flow of gas 38 from flow generator 36 through an outlet port 44 to an external conduit 144, and finally to patient interface 146. The example control machine pressure sensor 86 is connected to internal conduit 143 through an auto zero valve 87. Sensor 86 is a static pressure sensor used to monitor the pressure at or about outlet port 44 of ventilator 2. In addition, a monitor machine pressure sensor 88 is operatively coupled to internal conduit 143. Monitor machine pressure sensor 88 is also a static pressure sensor used to monitor the pressure at or about outlet port 44, in a redundant fashion. Other sensors suitable for use with ventilator 2 include, but are not limited to, temperature sensors 51 and 53, which are operatively coupled to the internal conduit 143 and are employed to monitor the temperature of the flow of gas 38 exiting flow generator 36, and a barometric pressure sensor 55 for measuring atmospheric pressure, for example, to allow for altitude adjustment of the calculated volumetric flow.

Although it is not employed in the passive exhalation without proximal pressure sensing configuration, which is shown in the example of FIG. 4, ventilator 2 also includes an active exhalation control assembly 90, which is employed when the ventilator is configured in the active exhalation configuration mode, as shown, for example, in FIG. 6. Finally, ventilator 2 includes a controller 98, which is schematically shown in FIGS. 4, 5 and 6. Controller 98 is electronically connected to, and is adapted to communicate with, each of the aforementioned components in order to selectively control the ventilator.

In the example of FIG. 4, ventilator 2 has one single external conduit 144 that interconnects outlet port 44 of the ventilator and patient interface 146. Accordingly, patient circuit 150 of ventilator 2 is a single-limb circuit, wherein the single external conduit 144 both delivers the flow of gas 38 from outlet port 44 to the patient interface 146 and ultimately to an airway 160 of patient 170 (partially shown in simplified form in FIGS. 4, 5, and 6), and carries exhalation gas 38", which is exhaled by patient 170 during the expiratory phase of the ventilatory cycle. Single-limb patient circuit 150 of FIG. 4 includes a passive exhalation device 152 (e.g. without limitation, a valve, orifice, port, or other vent arrangement) for venting (i.e., discharging) exhalation gas 38" to the atmosphere.

Although the patient interface 146 which is shown in the examples described herein is, for simplicity of illustration, a non-invasive mask 146, it will be appreciated that any known or suitable alternative patient interface, as defined herein, could be employed in any suitable configuration with the patient circuit 150 (FIG. 4), 150' (FIG. 5), 150" (FIG. 6). It will also be appreciated that the passive exhalation device 152 may be coupled to patient circuit 150, patient interface 146, or both.

Referring now to FIG. 5, the components of ventilator 2 are schematically shown as configured to provide passive exhalation with proximal pressure sensing. In this configuration, the ventilator components and the predetermined sensor configuration are largely the same as for the passive exhalation without proximal pressure configuration, previously described with respect to FIG. 4. However, in addition, a proximal pressure sensor 48 provided in housing 4 is configured to be in fluid communication with single external conduit 144' of single-limb patient circuit 150', via a probe 57 (e.g., a conduit), as defined herein, which is disposed proximate patient interface 146 that connects to line 56.

FIG. 6 shows a schematic illustration of ventilator 2 and components therefor in an active exhalation configuration. In such a configuration, ventilator 2 includes an alternate single-limb patient circuit 150" in fluid communication with the outlet port 44. Specifically, in addition to an external conduit 144", the single-limb patient circuit 150" also includes a proximal flow element 154 and an active exhalation device 156 (e.g., without limitation, valve). Proximal flow element 154 is a mechanical element positioned in the patient circuit generally proximate to patient interface 146", and is designed to produce a pressure drop when the flow of gas 38 and/or the exhalation gas 38" passes through it.

In an exemplary embodiment, active exhalation device 156 is a proportionally controlled pressure relief valve disposed in the single-limb patient circuit 150" and structured to provide low-resistance for enabling carbon dioxide flushing of the exhalation gas 38" during the expiratory phase of the ventilatory cycle. It will be appreciated that the active exhalation device 156 may be coupled to patient circuit 150", patient interface 146", or both. Active exhalation device 156 is structured to provide minimal exhalation resistance in order to meet anti-asphyxia requirements in the event of a loss of therapy (e.g., without limitation, a ventilator failure). Specifically, active exhalation device 156 includes an anti-asphyxia device 158 (shown in simplified form in FIG. 6) to meet such requirements. In one non-limiting embodiment, the anti-asphyxia device is a flapper valve 158 made, for example and without limitation, from rubber or another suitable material, which is structured to deflect, in the event of a failure or partial failure of ventilator 2, to uncover a corresponding aperture (not expressly shown) of the active exhalation device 156. Such aperture is in fluid communication with the atmosphere. Accordingly, flapper valve 158 ensures that patient 170 can, at a minimum, have the potential to inspire ambient air in the event of such failure of the ventilator 2.

In the example of FIG. 6, controller 98 is operatively coupled to the active exhalation control assembly 90 and, therefore, to active exhalation device 156. The active exhalation control assembly 90 is a pressure unit that regulates a diaphragm 157 (shown in simplified form in FIG. 6) of active exhalation device 156, in order to control bias flow as patient 170 exhales during the expiratory phase of the ventilatory cycle. The example active exhalation control assembly 90 includes a dump valve 91 structured to quickly reduce pilot pressure from diaphragm 157, thereby allowing it to fully open as patient exhalation is initiated, and a proportional valve 92 that, in combination with an orifice 93 provided between the two valves 91,92, controls the bias flow.

It can be appreciated that ventilator 2 is a small, lightweight, versatile ventilator that can be operated in a single-limb or dual-limb configuration and can provide both a pressure support therapy or a volume controlled therapy. Moreover, both the pressure support therapy or a volume based therapy can be delivered in a non-invasive system, e.g., a single limb system with intentional gas leaks such as that through the exhalation valve.

Table 1 below lists the specifications for an exemplary embodiment of the ventilator of the present invention.

TABLE 1

| Specification | Value |
| --- | --- |
| Weight | |
| Size | 4.5" × 6.88" × 9.5" |
| Ventilation Modes | A/C, SIMV, CPAP, S, S/T, T, PC, Flex |
| Tidal Volume (ml) | 50-2000 |
| Rate (bpm) | 0-60 |
| Peak Flow (lpm) | 3-150 |
| I-Time (second) | 0.2-5.0 |
| Volume Trigger Sensitivity (cmH$_2$O pressure, flow) | |
| E-Cycle (% peak flow) | |
| Pressure Support (cmH$_2$O) | 0-50 |
| Rise Time (second) | 0.1-0.6 |
| EPAP/PEEP (cmH$_2$O) | 4-46 |
| Internal Battery Runtime (hours) | 4.0 |
| Detachable Battery Runtime (hours) | 4.0 |
| Internal Battery Charge Time | 8 hours or less |

B. Porting System

It will be appreciated that the disclosed ventilator is operable among a plurality of different modes of operation including, but not limited to, a first mode for providing pressure support ventilation therapy to patient 170, and a second mode for providing volume control ventilation therapy to the patient. Furthermore, within such modes, ventilator 2 can have any suitable exhalation configuration such as, for example and without limitation, the aforementioned passive exhalation without proximal pressure sensing configuration of FIG. 4, the passive exhalation with proximal pressure sensing configuration of FIG. 5, and the active exhalation configuration of FIG. 6.

Switching ventilator 2 from one of these modes and/or configurations to another requires certain features of the ventilator 2 such as, for example and without limitation, the sensors and/or the patient circuit to be replaced and/or reconfigured. Traditionally, with a conventional ventilator, this has been a time-consuming endeavor that required a significant amount of disassembly and/or manipulation of the ventilator, or the use of a different ventilator altogether. This is because, prior to ventilator 2 of the present invention, all of the foregoing operating modes and configurations have not been available in one single ventilator device. As will now be discussed, one manner by which the disclosed ventilator overcomes these disadvantages is by providing a porting system 100 having a plurality of interchangeable porting blocks 102 (FIGS. 3, 7A, and 7B), 102' (FIG. 8), and 102" (FIG. 9) that enable ventilator 2 to be quickly and easily configured and/or reconfigured to the desired mode.

Specifically, porting system 100 includes the aforementioned sensors (e.g., without limitation, machine flow sensors 46, proximal pressure sensor 48, monitor flow sensor 50) and a plurality of probes (e.g., without limitation, conduits) therefor. For example, the exemplary machine flow sensor 46 includes a first machine flow probe 52 and a second machine flow probe 54, the proximal pressure sensor 48 includes at least one proximal pressure probe 56, and the monitor flow sensor 50 includes a first monitor flow probe 60 and a second monitor flow probe 62. Probes 52, 54, 56, 60, 62 are accessible at one common location on exterior surface 10 of ventilator housing 4. Each porting block 102 (FIGS. 3, 4, 7A and 7B), 102' (FIGS. 5 and 8), and 102" (FIGS. 6 and 9) includes a removable routing element 103 (FIGS. 3, 4, 7A, and 7B), 103' (FIG. 5), and 103" (FIG. 6) structured to be selectively coupled to ventilator housing 4 at or about the aforementioned common location, in order to configure probes 52, 54, 56, 57, 58, 59, 60, 62, 63, and 65 (all shown in FIG. 6) and thus the corresponding sensors 46, 48, 50, without requiring the ventilator 2 to be disassembled. This aspect of the invention will be further appreciated with reference to FIG. 3, wherein removable routing element 103 of porting block 102 is shown exploded away from ventilator housing 4.

Figure 2:
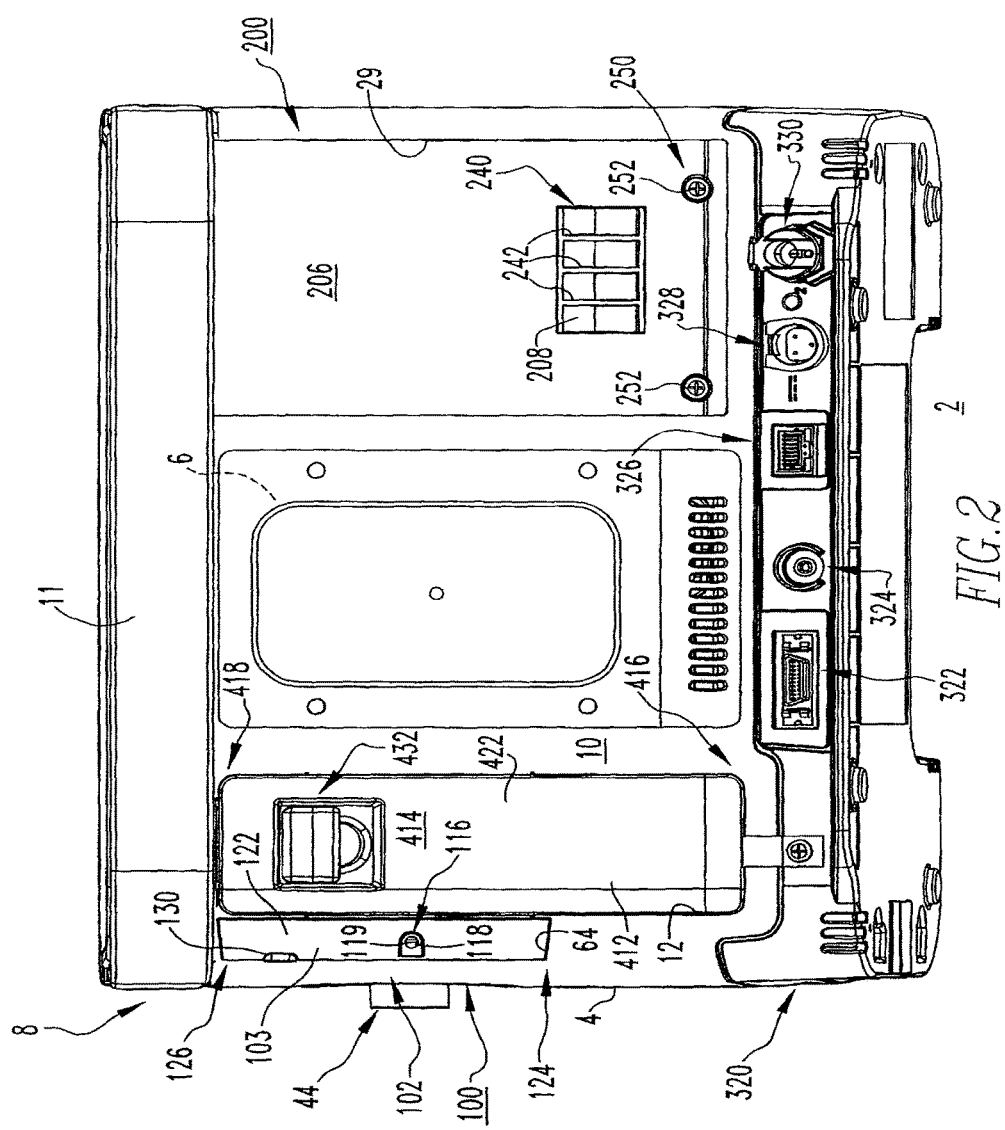
FIG. 2 is a back elevation view of the medical ventilator of FIG. 1.
Figure 3:
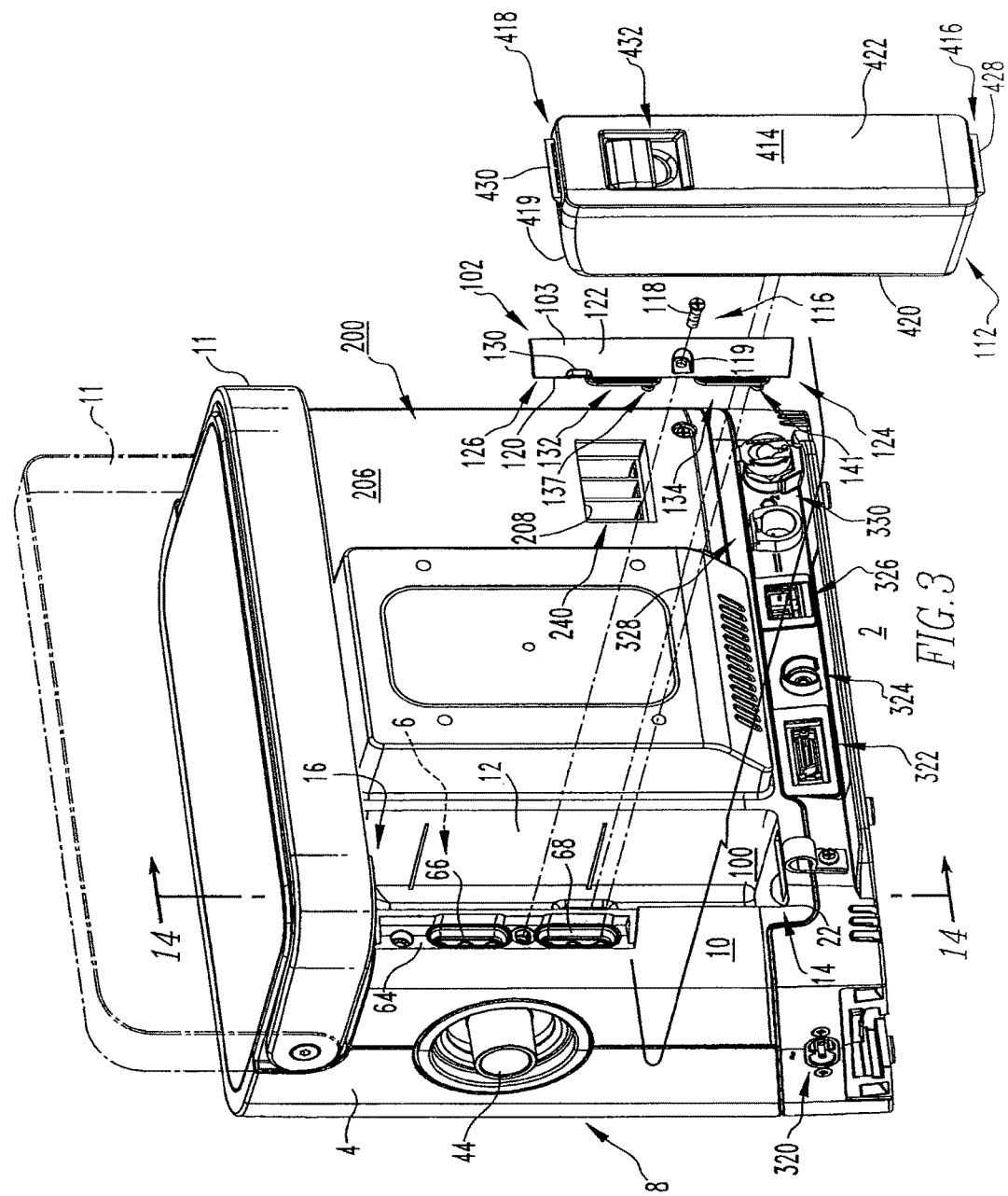
FIG. 3 is a partially exploded rear perspective view the medical ventilator of FIG. 1, showing a detachable battery pack and a porting system therefor.

A fastening mechanism 116 of porting system 100 is structured to fasten removable routing element 103 to housing 4, as shown in FIG. 2. The example fastening mechanism 116, which is also shown in FIG. 3, is a single fastener 118 structured to extend through a hole 119 of the removable routing element 103. As shown in FIG. 3, and also in FIGS. 7A and 7B, removable routing element 103 includes a first side 120, a second side 122 disposed opposite the first side, first and second opposing ends 124 and 126, and a plurality of passageways 104, 106, 108, 110, and 112 (FIG. 7B; see also passageways 104, 106, 108, 110, 112, and 114 schematically shown in FIG. 4), which extend from the first side 120 toward the second side 122. As employed herein, the term "passageway" refers to any known or suitable hole, throughway, conduit, or pathway that extends through at least a portion of an object, and expressly includes both active passageways, which are structured to allow for the passage of a fluid (e.g., gas) therethrough, and inactive passageways (i.e., closed passageways), which are structured to resist the passage of the fluid (e.g., gas) therethrough. When removable routing element 103 of the selected porting block (e.g., 102) is coupled to ventilator housing 4, passageways 104, 106, 108, 110, 112, and/or 114 thereof cooperate with probes 52, 54, 56, 60, 62, and/or 63 in order to establish the desired predetermined sensor configuration corresponding to the selected mode of operation of the ventilator.

For economy of disclosure, operation of only one of the porting blocks 102, will be described in detail. It will, however, be appreciated that the other interchangeable porting blocks (e.g., without limitation, porting blocks 102' and 102") of porting system 100 are employed in substantially the same manner. Referring again to FIG. 3, exterior surface 10 of ventilator housing 4 includes a recess 64 structured to receive removable routing element 103 of porting block 102. Thus, as shown in FIG. 2, second side 122 of removable routing element 103 is substantially flush with respect to exterior surface 10 of ventilator housing 4, adjacent recess 64, when removable routing element 103 is correctly inserted into recess 64. Hence, the interchangeable porting block design of the invention does not create undesirable protrusions that extend outwardly from ventilator housing 4.

In the example of FIG. 3, recess 64 includes first and second apertures 66 and 68 structured to receive first and second protrusions 132 and 134, respectively, which extend outwardly from first side 120 of removable routing element 103 (FIGS. 3, 7A and 7B). As shown in FIG. 7A and the sectional view of FIG. 7B, protrusions 132 and 134 preferably include seals 136 and 140, respectively. Seals 136 and 140 (see also O-ring seals 138 and 142) may be made from any known or suitable material such as, for example and without limitation, silicone rubber, and are structured to be respectively disposed on a corresponding portion of the protrusions 132, 134, 137, and 141 (best shown in FIG. 7B) in order to resist the unintentional leaking of the flow of gas 38 (FIGS. 4, 5 and 6) from between removable routing element 103 and ventilator housing 4. Removable routing element 103 in the example of FIGS. 7A and 7B includes nipples 137 and 141 extending outwardly from protrusions 132 and 134, respectively, and the seals include elongated seals 136 and 140 disposed in corresponding grooves of the protrusions 132 and 134, respectively, and O-ring seals 138 and 142 disposed in corresponding grooves of the nipples 137 and 141, respectively.

Removable routing element 103 also includes a finger tab 130 disposed between first and second ends 124 and 126 of the removable routing element 103, at or about second side 122 thereof. Finger tab 130 is structured to facilitate the removal of removable routing element 103 from recess 64 of the ventilator housing, for example, when it is desired to replace it with a different one of the removable routing elements 103' (FIGS. 5 and 8) or 103" (FIGS. 6 and 9), in order to change the configuration of the sensors of ventilator 2 for operation in a different mode. It will, however, be appreciated that any suitable alternative mechanism, other than the exemplary finger tab 130, could be employed in any suitable arrangement to facilitate the removal of removable routing element 103. It will also be appreciated that removable routing element 103 may have any known or suitable alternative configuration, without departing from the scope of the invention.

For example, FIGS. 8 and 9 show two non-limiting illustrative embodiments of different porting blocks 102' and 102", respectively, in accordance with the invention. As will be discussed, porting block 102' of FIG. 8 includes a removable routing element 103' structured to establish the predetermined sensor configuration schematically shown in FIG. 5, and porting block 102" of FIG. 9 includes a removal routing element 103" structured to establish the predetermined sensor configuration schematically shown in FIG. 6. Specifically, similar to porting block 102 of FIGS. 3, 4, 7A, and 7B, removable routing element 103' of porting block 102' has first and second protrusions 132' and 134' with first and second nipples 137' and 141', respectively.

Although they are not shown in FIG. 8, the removable routing element 103' is also contemplated as including seals such as those previously discussed with respect to FIGS. 7A and 7B. As will be discussed hereinbelow, the primary distinction of removable routing element 103' is with regard to the configuration of its passageways (see, for example, passageways 104', 106', 108', 110', 112', and 114' schematically shown in FIG. 5). One passageways 108' is structured to connect proximal flow sensor 48 to the patient circuit 150', as shown in FIG. 5. This passageway 108' extends through a port 109', which extends outwardly from the exterior surface of the removable routing element 103', as shown.

As will be discussed with respect to FIG. 6, passageways 104", 106", 108", 110", 112", and 114" (shown schematically in FIG. 6) of removable routing element 103" of FIG. 9 differ from those of removable routing element 103' (FIGS. 5 and 8) and removable routing element 103 (FIGS. 3, 4, 7A and 7B) and are thereby structured to establish the sensor configuration schematically illustrated in FIG. 6. Specifically, as shown in FIG. 9, removable routing element 103" includes first and second protrusions 132" and 134". First protrusion 132" includes one single nipple 137", and the second protrusion 134" includes three nipples 141", 145", and 147". In an exemplary embodiment, protrusions 132" and 134" and nipples 141", 145", and 147" include suitable seals (not shown in FIG. 9 for simplicity of illustration) such as those previously discussed with respect to FIGS. 7A and 7B. First, second and third passageways 104", 106", and 108" of removable routing element 103" extend through corresponding first, second, and third ports 105", 107", and 111", respectively, of removable routing element 103" to provide the desired probe/sensor connections.

In addition to the fact that porting blocks 102 (FIGS. 3, 4, 7A and 7B), 102' (FIGS. 5 and 8), and 102" (FIGS. 6 and 9) of porting system 100 can comprise any suitable configuration other than the three which are shown and described herein, it will be appreciated that they could also be made from any suitable material and by any suitable process or method. In one non-limiting example, interchangeable porting blocks 102, 102', 102" are single piece molded plastic components and, therefore, are relatively easy and inexpensive to manufacture.

Referring again to FIG. 4, the predetermined configuration of the sensors (e.g., without limitation, machine flow sensor 46, proximal pressure sensor 48, and monitor flow sensor 50) for the passive exhalation without proximal pressure sensing configuration and, in particular, the use of the removable routing element 103 to establish such configuration, will now be discussed. Specifically, in operation, when a determination is made to operate ventilator 2 in accordance with a particular mode and/or exhalation configuration, the patient circuit (e.g., without limitation, single-limb patient circuit 150) that corresponds to that mode and/or configuration is selected and coupled to outlet port 44 of ventilator 2. Alternatively, patient circuit 150 can be configured or reconfigured as desired, for example by exchanging one exhalation device (e.g., a passive exhalation device 152) with another exhalation device (e.g., a different passive exhalation device; an active exhalation device 156 as shown, for example, in FIG. 6) and/or by attaching or changing patient interface 146. In other words, single outside conduit 144 of patient circuit 150 could remain attached to outlet port 44 of ventilator 2, with the exhalation device 156 and/or the patient interface 146 being selectively coupled to the conduit 144, for example by one or more quick-change fittings (e.g., without limitation, a slip fitting) (not expressly shown). Thus, patient circuits that are both removable and replaceable or interchangeable in their entirety, and patient circuits that are selectively configurable and/or reconfigurable, in part, are within the scope of the invention.

After selecting or configuring the patient circuit 150 (FIG. 4), 150' (FIG. 5), or 150"(FIG. 6), the corresponding porting block 102 (FIGS. 3, 4, 7A and 7B), 102' (FIGS. 5 and 8), or 102"(FIGS. 6 and 9) is then selected and attached to ventilator housing 4 (best shown in FIG. 2). As previously noted, to establish the various predetermined sensor configurations, each of the removable routing elements 103 (FIGS. 3, 4, 7A, 7B), 103' (FIGS. 5 and 8) and 103" (FIGS. 6 and 9) has a different arrangement of passageways, which are structured to selectively cooperate with the sensor probes in a predetermined manner. Specifically, in the example of FIG. 4, the removable routing element 103 includes first, second, third, fourth, and fifth active passageways, 104, 106, 108, 110, and 112, and one inactive passageway 114. First active passageway 104 cooperates with second active passageway 106 in order to connect first machine flow probe 52 to first monitor flow probe 60. The third active passageway connects the proximal pressure sensor 48 to the ambient atmosphere, for example, via a single proximal pressure probe 56. Fourth and fifth active passageways 110, 112 cooperate with one another to connect second machine flow probe 54 to the second monitor flow probe 62, as shown. Finally, because the active exhalation control assembly 90 is not employed in the passive exhalation without proximal pressure sensing configuration of FIG. 4, active exhalation control probe 63 is connected to passageway 114, which is inactive (blocked).

Accordingly, it will be appreciated that all of the sensors are configurable to the desired predetermined configuration corresponding to the selected mode of operation of ventilator 2, merely by attaching the appropriate interchangeable porting block (e.g., without limitation, 102) to ventilator housing 4. It will, however, be appreciated that the exact arrangement of passageways of the removable routing elements 103 (FIGS. 3, 4, 7A and 7B), 103' (FIGS. 5 and 8), and 103" (FIGS. 6 and 9) of the porting blocks 102 (FIGS. 3, 4, 7A and 7B), 102' (FIGS. 5 and 8), and 102" (FIGS. 6 and 9) is not meant to be a limiting aspect of the invention. The porting system of the present invention allows the same ventilator sensors to be reconfigured quickly and easily by simply interchanging porting blocks 102 (FIGS. 3, 4, 7A and 7B), 102' (FIGS. 5 and 8), 102" (FIGS. 6 and 9), i.e., without having to add or remove other sensing elements.

As shown in FIG. 5, and as previously noted, the components of ventilator 2 are arranged substantially similarly for the passive exhalation with proximal pressure sensing configuration as for the passive exhalation without proximal pressure sensing configuration discussed with respect to FIG. 4. The primary difference is the inclusion of a second proximal pressure probe 57, which is in fluid communication with the external conduit 144 of patient circuit 150', proximate patient interface 146. Removable routing element 103' of second interchangeable porting block 102' is structured to accommodate this proximal pressure probe 57. Specifically, similar to removable routing element 103, removable routing element 103' includes first, second, third, fourth, and fifth active passageways 104', 106', 108', 110', and 112', and one inactive passageway 114'. The first and second active passageways 104' and 106' cooperate in order to connect first machine flow probe 52 to first monitor flow probe 60. However, unlike third passageway 108 of removable routing element 103, which connected proximal pressure probe 56 to the atmosphere, third passageway 108' of removable routing element 103' connects first proximal pressure probe 56 to second proximal pressure probe 57, as shown. Fourth and fifth active passageways 110' and 112' connect second machine flow probe 54 and second monitor flow probe 62, and active exhalation probe 63 is connected to inactive passageway 114'.

Referring now to FIG. 6, when ventilator 2 and components therefor are configured for active exhalation, single-limb patient circuit 150" additionally includes the aforementioned proximal flow element 154 and active exhalation device 156. Accordingly, a number of additional probes such as, for example and without limitation, third and fourth proximal pressure probes 58 and 59 and an active exhalation device probe 65, are required. The configuration of these and other probes is established by third removable routing element 103" of interchangeable porting block 102" and, in particular, first, second, third, and fourth active passageways 104", 106", 108", and 110" and first and second inactive passageways 112" and 114" thereof.

First active passageway 104" connects first monitor flow probe 60 to second proximal pressure probe 57, second active passageway 106" connects first proximal pressure probe 56 to fourth proximal pressure probe 59, and third active passageway 108" connects second monitor flow probe 62 to third proximal pressure probe 58. In this manner, proximal pressure probes 57 and 58 communicate with sensor 50 to monitor the flow of gas 38, 38" on opposing sides of the proximal flow element 154. Fourth active passageway 110" connects first active exhalation control probe 63 to active exhalation device probe 65. Thus, in this configuration, active exhalation control assembly 90 is actively employed via controller 98 to monitor and control active exhalation device 156. Machine flow sensor 46 and first and second machine flow probes 52, 54 are not required in this configuration and, therefore, are coupled to first and second inactive passageways 112" and 114", respectively.

In view of the foregoing, it will be appreciated that the invention enables a single ventilator 2 to be quickly and easily configured or reconfigured to provide various types of ventilation therapy, without requiring the ventilator to be disassembled or replaced. Particularly unique is the ability of ventilator 2 to provide volume control ventilation therapy (also referred to volume ventilation) to patient 170 using the aforementioned passive exhalation device 152 (e.g., without limitation, passive exhalation valve, orifice). Effective patient ventilation using this combination was previously thought to be substantially impossible.

Specifically, it is somewhat counterintuitive to allow for the passive escape of gas 38" to the atmosphere when it is vitally important to accurately maintain a desired inhalation volume of gas 38 for the patient as is often the case in volume control, life support situations. Accordingly, known volume control (i.e., life support) ventilation systems (not shown) have traditionally required an active exhalation device which serves as part of a dual-limb patient circuit (i.e., the patient circuit includes at least two external conduits, one for patient inhalation during the inspiratory phase of the ventilatory cycle and one for patient exhalation during the expiratory phase of the ventilatory cycle). This tended to result in a ventilator design that was larger and more complex than desired. As such, the ventilators were generally not conducive for use outside of a hospital, designated care center or other facility where the ventilator could be closely monitored and maintained by a doctor, medical specialist, or trained personnel.

The ability of the ventilator of the present invention to provide volume control ventilation therapy using passive exhalation overcomes these disadvantages, and others, by providing a single substantially mobile, lightweight ventilator 2, which enables the patient to move relatively easily from one location to another while continuing to receive the appropriate ventilation therapy. Accordingly, the disclosed ventilator affords the patient the opportunity to maintain a relatively active lifestyle.

More specifically, as previously discussed and referring, for example to FIG. 5, patient circuit 150' of the example ventilator is preferably a single-limb circuit 150' including a single external conduit 144', wherein the single-limb circuit may comprise a separate, self-contained assembly that is selectively connectable to ventilator 2 at outlet port 44 thereof, or it may be selectively configurable with components such as patient interface 146 and passive exhalation device 152 being selectively connectable to single conduit 144'. In any event, single conduit 144' interconnects outlet port 44 of ventilator 2 and patient interface 146. Passive exhalation device 152 is coupled to single conduit 144' proximate patient interface 146. When operating in a controlled volume (volume ventilation) mode, controller 98 of ventilator 2, which is operatively coupled to flow generator 36, is adapted to selectively control flow generator 36 to generate the flow of gas 38 having an inhalation volume, also referred to as an inspiratory tidal volume. The present invention also contemplates providing a volume ventilation in which the inspiratory flow profile is provided over a predetermined inspiratory time.

Single-limb patient circuit 150' delivers the flow of gas 38 having the inhalation volume to airway 160 of patient 170 during the inspiratory phase of the ventilatory cycle. In the example shown and described herein, both the inhalation volume of the flow of gas 38 and exhalation gas 38" are transported within the single conduit 144' of the single-limb patient circuit 150'. It will be appreciated that a function of passive exhalation device 152 is to flush carbon dioxide, which is present in exhalation gas 38" exhaled by the patient, to the atmosphere. Subsequently, a fresh inhalation volume of a flow of gas 38 may be delivered to the patient during the inspiratory phase of the next ventilation cycle.

It will be appreciated that the particular inhalation volume, or volume ventilation, prescribed for the patient is dependent on a variety of different factors including, but not limited to, the type of disease from which the patient suffers, and the stage of progression of the disease. In one non-limiting embodiment, ventilator 2 and, in particular, controller 98 therefor, is adapted to selectively adjust flow generator 36, as necessary, to cause the flow of gas 38 to have the desire inhalation volume, which is delivered to the patient during the inspiratory phase of the ventilatory cycle. This can be done automatically. Alternatively, ventilator 2 can be programmed using the aforementioned user interface 300, either by the patient himself/herself or preferably by the doctor or caretaker. During the expiratory phase of the ventilatory cycle, at least a portion of the exhalation gas 38", which is exhaled by the patient 170, is discharged to the atmosphere by passive exhalation device 152. Accordingly, among other benefits, ventilator 2 provides effective volume control ventilation therapy, using passive exhalation such that neither the aforementioned double-limb patient circuit (not shown) nor the active exhalation device of known volume control ventilation systems (not shown) is required.

Controller 98 of ventilator 2 is preferably adapted to also provide leak compensation. For example and without limitation, controller 98 may be adapted to execute a suitable leak compensation routine in order to detect a leak in the patient circuit 150' and, responsive to detecting the leak, make an appropriate adjustment with respect to the operation of the ventilator 2. One non-limiting example of a suitable leak compensation routine is the Autotrack® software program, which is commercially available from the assignee of the present invention. Examples of leak estimation/compensation techniques are provided in U.S. Pat. Nos. 5,148,802; 5,313,937; 5,433,193; 5,632,269; 5,803,065; 6,029,664; 6,626,175; 6,360,741; 6,920,875; 6,948,497; and 7,100,607, the contents of which are incorporated herein by reference.

Alternatively, the present invention contemplates providing a known/intended leak or a fixed leak device or exhaust port that has a known leak rate to pressure relationship. This relationship can be used to determine the leak rate for any given pressure.

Additionally, the present invention contemplates providing leak compensation for unknown (unintended) leaks, such as leaks attributed to the patient-to-ventilator circuit interface, leaks at the cuff, mouth, mask, etc. These unknown/unintended leaks are compensated for using a different programmed response than known leaks, i.e., leaks assigned to the known or fixed (intended) leak device. This different programmed response can include (w/o limitation) leak limits, assumed pressure to leak relationships, and single or multiple time constants that are separate and distinct from the relationships employed to model the known or intended leak. This programmed response can be used to adjust the flow from the ventilator to ensure that the patient receives the prescribed tidal volume in the event of certain anticipated physiological or use case changes in the patient to ventilator circuit interface.

In general, responsive to detecting or estimating a leak (intended, unintended, or both) of the flow of gas 38, controller 98 is adapted to selectively adjust flow generator 36 to cause the flow of gas to have the desired inhalation volume, which is delivered to the patient during the inspiratory phase of the ventilatory cycle.

The expiratory phase of the ventilatory cycle has a tidal volume. At least some of the aforementioned sensors such as, for example, proximal sensor 48, can be employed in fluid communication with the patient circuit (see, for example, patient circuit 150' of FIG. 5), proximate passive exhalation device 152, to determine the tidal volume of the exhalation gas 38". Responsive to determining the tidal volume, ventilator controller 98 selectively adjusts flow generator 36 to generate a flow of gas 38 having a desired inhalation volume, which is to be delivered to patient 170 during the inspiratory phase of the next ventilatory cycle.

Among other benefits, the adaptability of ventilator 2 enables the same ventilator to be employed throughout the progression of the patient's disease. For example, in one non-limiting circumstance, patient 170 might progress from a condition that initially requires only intermittent pressure support ventilation therapy to eventually requiring substantially constant volume control ventilation therapy. Such a progression may occur relatively slowly over an extended period of time. Accordingly, a combination of ventilation therapies may be required throughout the disease progression. The disclosed ventilator is well suited to accommodate such circumstances and to meet the ventilation needs of such a patient, regardless of what those needs may be and how they may change.

Specifically, in one non-limiting embodiment, ventilator controller 98 is adapted to selectively switch ventilator 2 among the volume control and pressure support modes. Additionally, if necessary, patient circuit (e.g., 150 (FIG. 4), 150'(FIG. 5), or 150"(FIG. 6)) can relatively quickly and easily be exchanged (i.e., replaced) or reconfigured to provide either passive exhalation, for example, as shown in FIGS. 4 and 5, or active exhalation, for example, as shown in FIG. 6. Additionally, various patient interfaces 146 can be selectively employed, as necessary, without requiring significant adjustment or replacement of the ventilator 2.

C. Inlet Airflow Assembly

Figure 10:
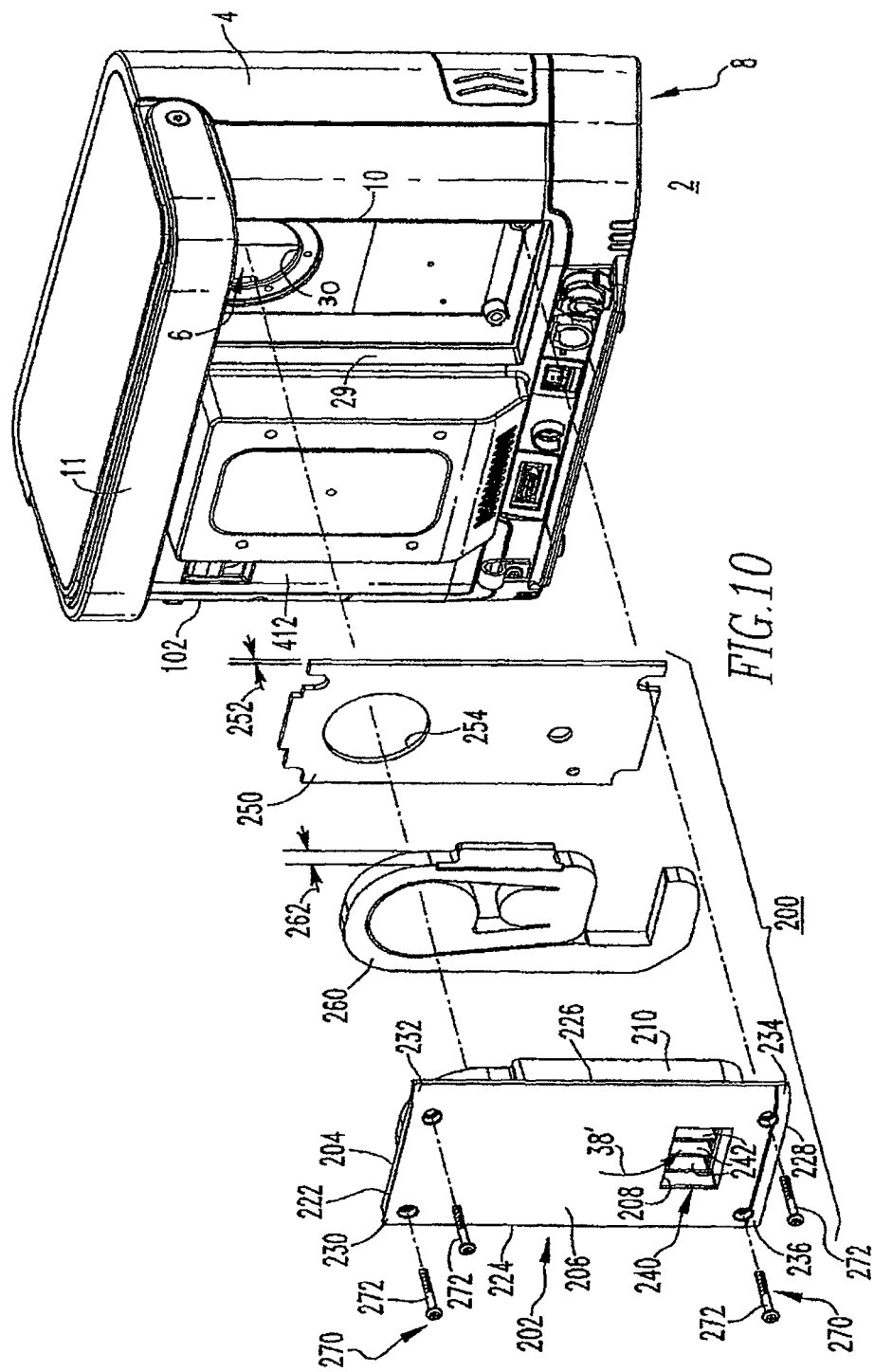
FIG. 10 is a partially exploded isometric view of the back of a medical ventilator and an intake airflow assembly therefor.

FIG. 10 shows an inlet airflow assembly 200 for ventilator 2. Among other benefits, inlet airflow assembly 200 is of a modular design and is selectively removable from ventilator housing 4 without requiring the remainder of ventilator 2 to be disassembled. Accordingly, the remainder of the ventilator can be relatively quickly, easily, and inexpensively serviced. For example, ventilator 2 can be quickly and effectively disinfected and/or sterilized. As will be discussed, this may be accomplished by replacing the entire used inlet airflow assembly 200 with a new inlet airflow assembly 200, for example, in the form of a replacement kit, or inlet airflow assembly 200 could be removed and at least some of the components (e.g., without limitation, cover member 202, discussed hereinbelow) thereof could be cleansed using any suitable approved disinfecting or sterilization procedure, while other components (e.g., without limitation, filtering member 250 and/or filtering member 260, discussed hereinbelow) of the assembly 200 could be replaced.

The ability to quickly and easily replace filtering members 250 and 260 is highly desirable because such members, which can comprise any known or suitable gasket, baffle, noise attenuating device and/or filtering media, are commonly made from materials such as, for example and without limitation, open cell foam, which can undesirably collect and retain debris, germs and bacteria. As such, members 250 and 260 must be replaced or suitably disinfected, in order to properly sterilize ventilator 2. Without the disclosed modular inlet airflow assembly 200, it would be necessary to disassemble a significant portion of ventilator 2, or to replace it entirely with a new ventilator, in order to achieve the requisite level of sterilization. Disassembling the ventilator is undesirably time-consuming, and is not a suitable option for the average patient and/or caretaker. It also requires an extended amount of downtime during which the ventilator is inoperable. The only other option, which is to replace the ventilator entirely, is cost-prohibitive and presents the potential for problematic issues such as, for example, lack of availability of a suitable replacement ventilator or delay in receiving the replacement, reconfiguring the replacement, etc.

The disclosed inlet airflow assembly 200 overcomes these and other disadvantageous by providing a removable modular assembly including a cover member 202, which is structured to be selectively coupled to ventilator housing 4 at or about an inlet port 30 (FIG. 10) of the ventilator. Cover member 202 has first and second opposing sides 204 and 206 and an inlet aperture 208 structured to deliver a gas (generally indicated by reference 38' in FIGS. 10 and 11) to inlet port 30. Inlet airflow assembly 200 disclosed and described herein includes two of the aforementioned filtering members 250 and 260. However, it will be appreciated that any alternative number and/or configuration of filtering members could be employed without departing from the scope of the invention.

Inlet airflow assembly 200 preferably includes a fastening mechanism 270 such as, for example and without limitation, four screws 272 as shown in the example of FIG. 10. Fastening mechanism 270 is structured to fasten cover member 202 to ventilator housing 4, thereby securing cover member 202 and filtering members 250 and 260 with respect thereto. Fastening mechanism 270 also enables the relatively quick and easy removable and/or replacement of inlet airflow assembly 200 or a portion thereof, for example, by simply loosening and/or removing screws 272. Of course, the present invention contemplates other configurations for fastening mechanism 270. For example, a snap fit, tongue and groove, friction fit, slotted arrangement or any other suitable fastening technique can be used to couple cover member 202 to ventilator housing 4.

As shown in FIG. 10, exterior surface 10 of ventilator housing 4 includes a pocket 29, which extends inwardly from the exterior surface to receive inlet airflow assembly 200. When inlet airflow assembly 200 and, in particular, cover member 202 therefor, is disposed within pocket 29, second side 206 of the cover member is substantially flush with respect to exterior surface 10 of ventilator housing 4 adjacent the pocket. The flush nature of the inlet airflow assembly, when it is attached to the ventilator housing, can be appreciated with respect to FIGS. 2 and 3, which show the inlet airflow assembly fully mounted on the ventilator housing.

As with the substantially flush porting block 102, previously discussed hereinabove, the flush design of inlet airflow assembly 200 overcomes the disadvantages commonly associated with protrusions that extend outwardly from the ventilator housing 4. In other words, the removable inlet airflow assembly 200 and, for that matter, the other removable or otherwise detachable features (e.g., without limitation, porting block 102, detachable battery pack 412, discussed hereinbelow) of ventilator 2 do not undesirably interfere with the overall form factor (i.e., overall shape of the exterior surface 10 of the ventilator housing 4) of the ventilator.

Figure 11:
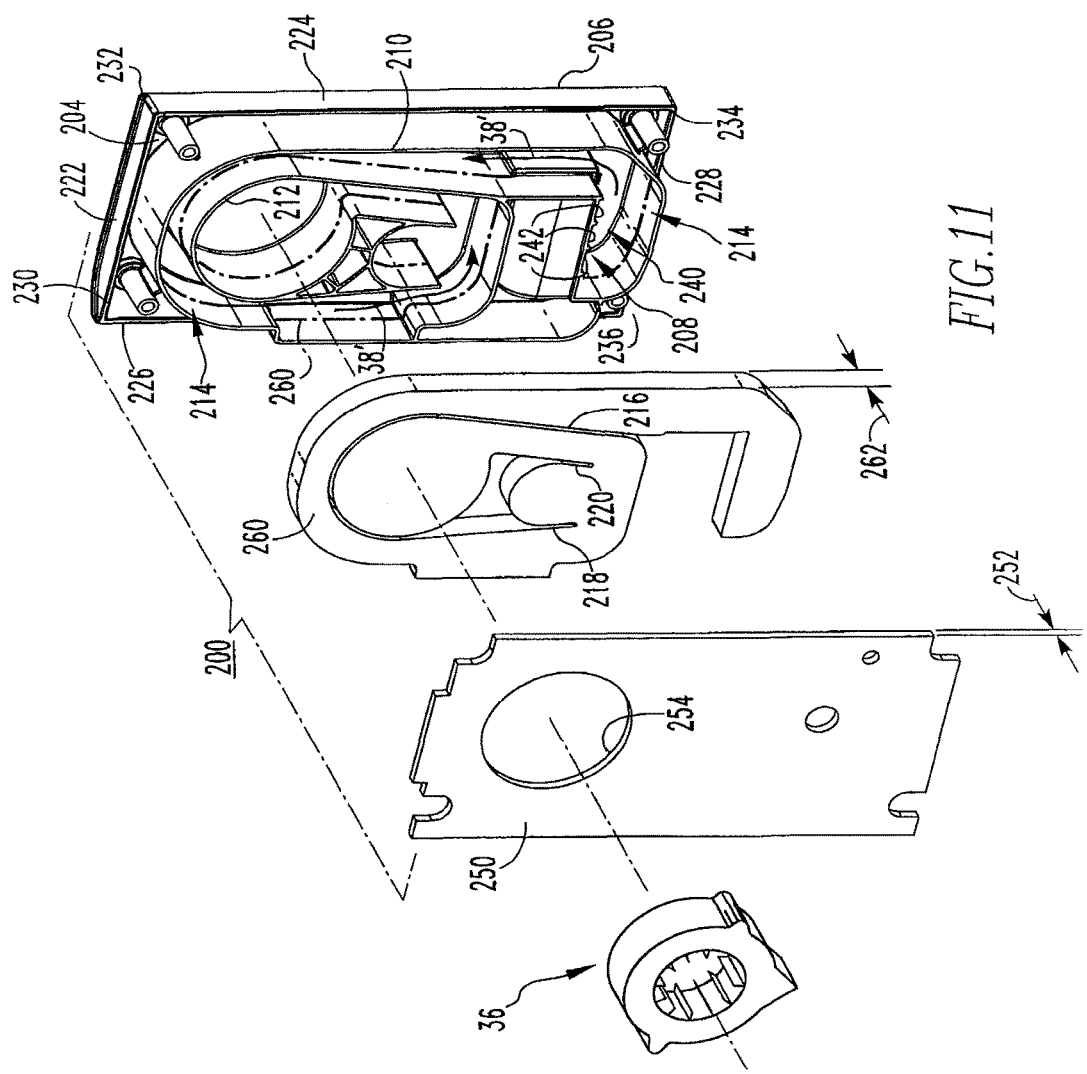
FIG. 11 is an exploded isometric view of the intake airflow assembly of FIG. 10, also showing the flow generator of the medical ventilator.

As best shown in FIG. 11, cover member 202 of inlet airflow assembly 200 includes a plurality of walls 210 and 212, which extend substantially perpendicularly outwardly from first side 204 of the cover member. Accordingly, when cover member 202 is disposed within pocket 29 (FIGS. 2 and 3), walls 210 and 212 of the cover member are structured to extend into pocket 29 (FIG. 10) in order to direct gas 38' toward inlet port 30 of ventilator 2. Specifically, walls 210 and 212 form an inlet airflow path 214, which extends from inlet aperture 208 of cover member 202 toward inlet port 42 of ventilator 2.

Cover member 202 in the example shown in FIG. 11 is generally rectangular shaped and includes four peripheral edges 222, 224, 226, 228 and four corners 230, 232, 234, and 236. Each of the four screws 272 of the example fastening mechanism 270 extends through a corresponding one of corners 230, 232, 234, and 236, as shown in the exploded view of FIG. 10. It will, however, be appreciated that any known or suitable alternative fastening mechanism could be employed in any suitable alternative number and/or configuration, without departing from the scope of the invention.

Walls 210 and 212 of the example cover member 202 include an outer wall 210 disposed proximate peripheral edges 222, 224, 226, and 228, and an inner wall 212 spaced inwardly from outer wall 210, as shown. Inner wall 212 also extends around at least a portion of inlet port 42 (FIG. 10) of ventilator 2 (FIG. 10). Thus, an inlet airflow path 214 is disposed between outer wall 210 and inner wall 212 of cover member 202. Cover member 202 further includes a duct 240 (partially shown) (also shown in FIGS. 2, 3 and 10), which extends inwardly from first side 204 of cover member 202 at or about inlet aperture 208 thereof, in order to direct gas 38' into inlet airflow path 214. The example duct 240 further includes a plurality of louvers 242, to further direct and control the inlet gas 38', as desired.

At least one of the number of filtering members 250 and 260 of inlet airflow assembly 200 is a filter element that is structured to be disposed between the walls 210 and 212 of cover member 202, in inlet airflow path 214. Thus, gas 38' flows through filter element 260, as shown in phantom line drawing in FIG. 11. As previously discussed, filter element 260 may be made from any known or suitable filtering media such as, for example and without limitation, foam (e.g., without limitation, open cell foam). The example filter element 260 includes a plurality of slots 216, 218, and 220 extending therethrough. As shown in phantom line drawing in FIG. 11, when filter element 260 is disposed in the assembled position, portions of walls 210 and 212 of cover member 202 extend through the corresponding slots 216, 218, and 220 of filter element 260. In this manner, the position of filter element 260 is maintained with respect to cover member 202. It should be noted, however, that filter element 260 is also preferably selectively detachable from over member 202, for example in order to be replaced or suitably disinfected, as previously discussed.

As noted previously, inlet airflow assembly 200 includes first and second filtering members 250 and 260. First filtering member 250 is disposed adjacent ventilator housing 4, and second filtering member 260 is disposed between first filtering member 250 and first side 204 of cover member 202. First and second filtering members 250 and 260 have first and second thicknesses 252 and 262, respectively, wherein second thickness 262 of second filtering member 260 is greater than first thickness 252 of first filtering member 250. It will, however, be appreciated that a wide variety of other filtering member embodiments (not shown) are within the scope of the invention. The example first filtering member 250 preferably functions, at least in part, as a gasket for resisting undesired leaking of gas 38' from between cover member 202 and ventilator housing 4. First filtering member 250 also includes a hole 254, which is structured to align within inlet port 42 of ventilator 2 and, in particular, with flow generator 36 (shown in simplified form in FIG. 11), when filter member 250 overlays first side 204 of cover member 202.

Accordingly, the disclosed exemplary embodiment of inlet airflow assembly, which in one non-limiting embodiment of the invention, can comprise a kit containing a new (i.e., replacement) cover member 202 and suitable filtering members (e.g., without limitation, first and second filtering members 250 and 260), enables ventilator 2 to be quickly, easily, and inexpensively sterilized or otherwise serviced, without requiring the substantial disassembly and/or replacement of the ventilator.

D. Power Prioritization and Detachable Battery Pack

Figure 12:
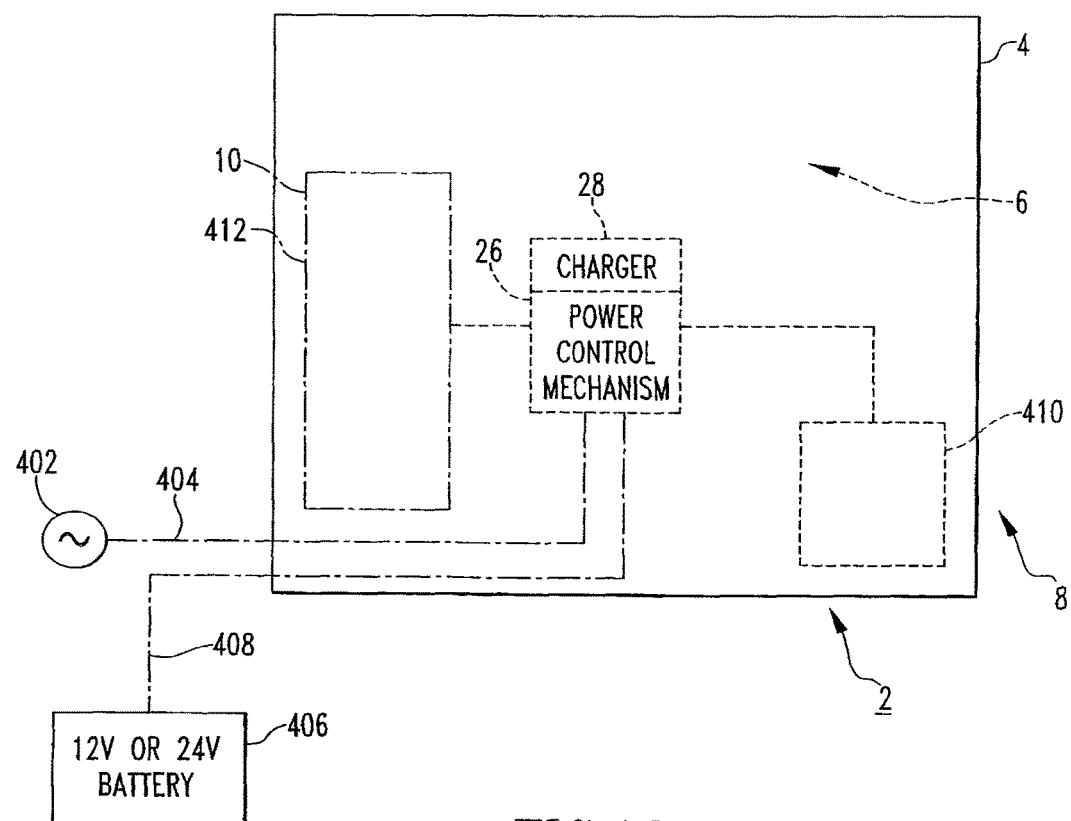
FIG. 12 is a schematic view of a power supply system for a medical ventilator.

FIG. 12 shows a schematic representation of ventilator 2 and various sources of power therefor, in accordance with the principles of the invention. It will be appreciated that, for simplicity of illustration, internal components of ventilator 2 and the details thereof, have not been shown in FIG. 12. The various sources of power, which will now be described, are employable to provide power to any known or suitable component of the ventilator and/or a number of accessories (e.g., without limitation, a humidifier; an oxygen blender; a pulse oximeter; a carbon dioxide monitor) therefor.

In the example shown and described herein, power is supplied to ventilator 2 by way of the following four sources of power:

1) an alternating current (AC) power source 402 (schematically shown in simplified form in FIG. 12) which is electrically connectable to the ventilator 2 using a first power connection 404 (e.g., without limitation, a power cord), 2) a lead acid battery 406 such as, for example and without limitation, a 12 VDC car battery or 24 VDC truck battery, which is electrically connectable to ventilator 2 using a second power connection 408 (e.g., without limitation, a battery connector), 3) an internal battery pack 410 (shown in simplified form in hidden line drawing in FIG. 12) disposed within the interior 6 of the ventilator housing 4, and 4) a detachable battery pack 412 (shown in simplified form in phantom line drawing in FIG. 12). As will be discussed, the detachable battery pack 412 is removably coupled to exterior surface 10 of ventilator housing 4.

Each of the four power sources 402, 406, 410, and 412 is electrically connected to a power control mechanism 26 (shown in simplified form in hidden line drawing in FIG. 12), which is adapted to selectively cause power to be supplied to ventilator 2 from power sources 402, 406, 410, and 412 in accordance with a predetermined hierarchy, described in greater detail hereinbelow.

Sources of power 402, 406, 410, and 412 and the hierarchy for supplying power to ventilator 2 employing the same, greatly improves upon known ventilators which, at best, are structured to operate using one of three sources of power, namely an AC power source, a lead acid battery, or an internal rechargeable battery pack. Such ventilators (not shown) fail to further include detachable battery pack 412 of the invention. As will be discussed, among other advantages, detachable battery pack 412 improves the portability of the ventilator, thereby improving the ability of the patient to be mobile and to maintain his/her lifestyle while receiving ventilation therapy.

It will be appreciated that ventilator 2 could be adapted to be electrically connectable to any known or suitable AC power source 402 such as, for example and without limitation, a 110 VAC power source or a 220 VAC power source. The electrical connection between the AC power source 402 and ventilator 2 may be made by way of any known or suitable power connection 404. Similarly, it will be appreciated that the exemplary lead acid battery 406 could alternatively comprise any known or suitable battery of any suitable voltage and/or chemistry, without departing from the scope of the invention. Lead acid battery 406 can also be electrically connected to ventilator 2 using any known or suitable power connection 408.

It will further be appreciated that internal battery pack 410 and detachable battery pack 412 are preferably rechargeable. In accordance with one non-limiting embodiment of the invention, each of these battery packs 410 and 412 comprises a number of lithium ion batteries (see, for example, lithium ion batteries 424 of detachable battery pack 412, shown in the sectional view of FIG. 14) and, as shown in simplified form, in FIG. 12, the example power control mechanism 26 further includes a charger 28. Accordingly, when ventilator 2 is electrically connected to AC power source 402 or lead acid battery 406, and internal battery pack 410 is not fully charged, power source 402 and/or 406 powers charger 28 to charge battery pack 410. As will be discussed, charger 28 can also be adapted to charge detachable battery pack 412, if it is not fully charged.

Detachable battery pack 412 is connectable to ventilator housing 4 in only one predetermined orientation and, when it is disposed in such orientation, it does not undesirably protrude from exterior surface 10 of ventilator housing 4. This advantageously simplifies the process of employing detachable battery pack 412 to power the ventilator by making it abundantly clear for the patient or caregiver how to properly insert the detachable battery pack. Furthermore, the fact that detachable battery pack 412, once inserted in the appropriate orientation does not protrude from the exterior surface of the ventilator housing advantageously provides the ventilator housing with a generally uniform form factor (i.e., overall shape of the exterior surface 10 of the ventilator housing 4), thereby eliminating the disadvantages commonly associated with protrusions. For example and without limitation, by being substantially flush with the rest of the housing 4 unintentional bumping into surrounding objects with a protrusion of housing 4 is avoided, and ventilator 2 is less awkward and/or difficult to hold and/or transport because it has a relatively uniform shape (see FIGS. 1, 2 and 3) and associated weight distribution. The flush nature of the detachable battery pack 412 can be further appreciated with reference to FIGS. 2 and 14, and the unique single-orientation aspect of detachable battery pack 412 can be further appreciated with respect to the sectional view of FIG. 14.

Figure 13:
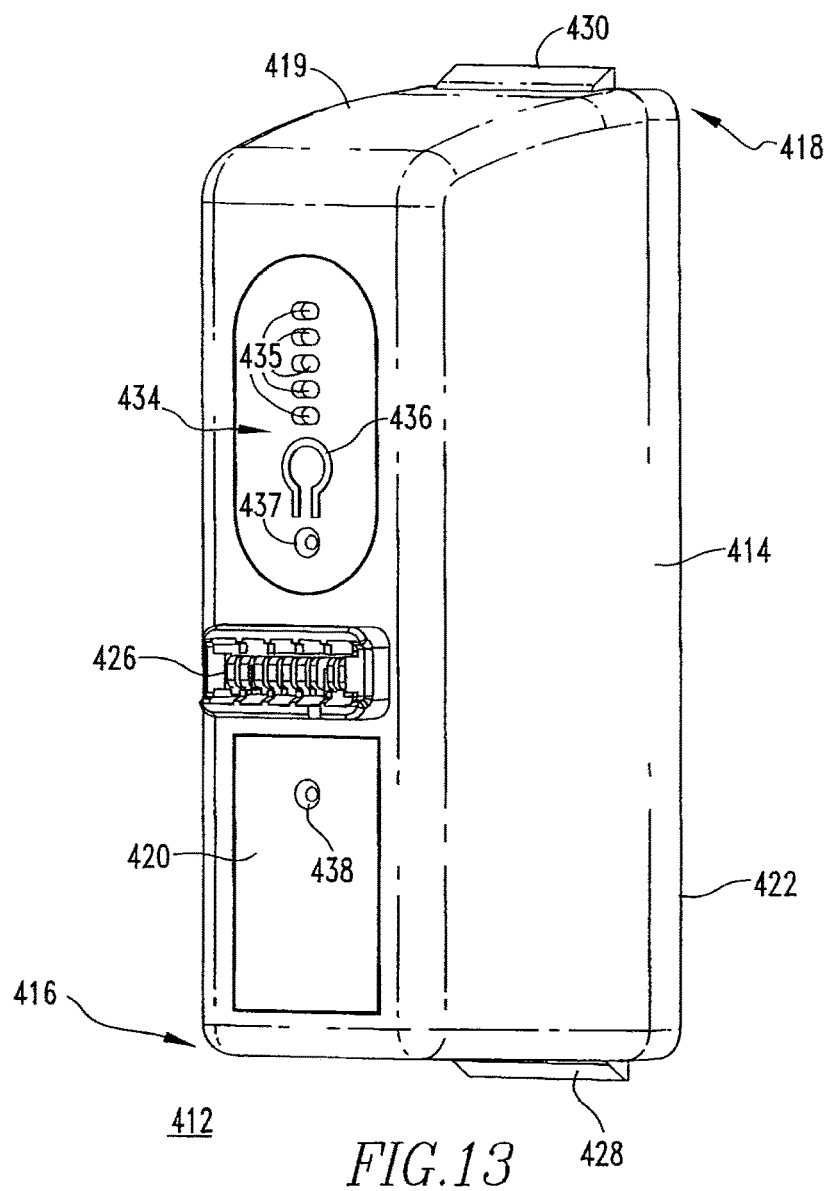
FIG. 13 is an isometric view of the detachable battery pack of FIG. 3.
Figure 14:
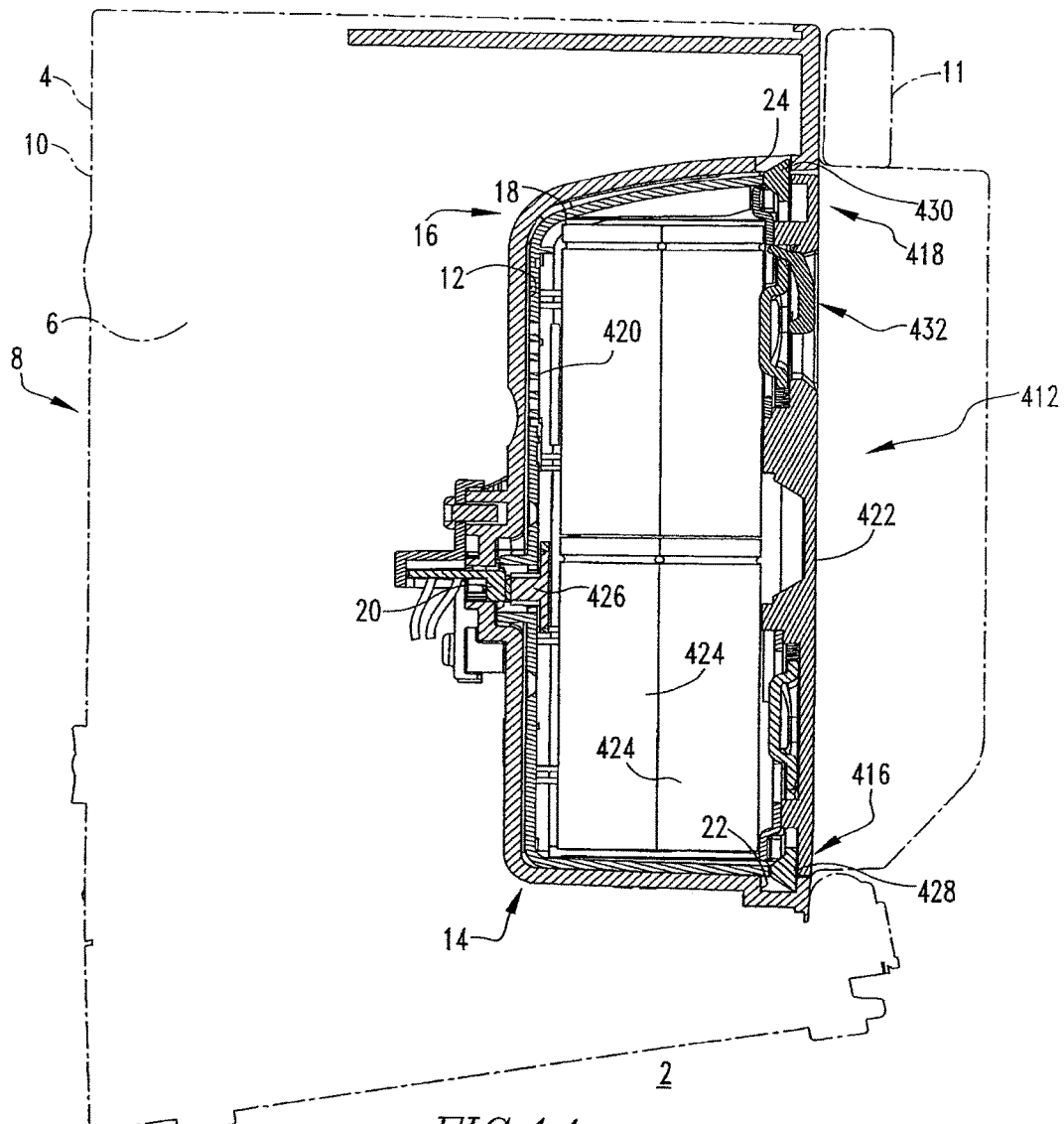
FIG. 14 is a sectional view taken along line 14-14 of FIG. 3.

More specifically, as shown in FIGS. 3, 13, and 14, detachable battery pack 412 includes an enclosure 414 having a first end 416, a second end 418 disposed opposite and distal from the first end 416, a first side 420, and a second side 422. As shown in FIGS. 2 and 14, only when detachable battery pack 412 is disposed in the predetermined orientation within a cavity 12 defined in ventilator housing 4, is second side 422 of enclosure 414 substantially flush with respect to exterior surface 10 of the ventilator housing adjacent the cavity, as previously discussed.

A number of batteries 424 (four are shown in the sectional view of FIG. 14) such as, for example and without limitation, the aforementioned lithium ion batteries, are enclosed by enclosure 414, and an electrical connector 426, which is electrically connected to batteries 424, extends outwardly from first side 420 of enclosure 414, as shown in FIGS. 13 and 14. Electrical connector 426 of detachable battery pack 412 is structured to be electrically connected to a corresponding electrical connector 20 disposed within cavity 12 of ventilator housing 4, as shown in FIG. 14.

When detachable battery pack 412 is inserted into cavity 12 of ventilator housing 4 in the correct orientation, electrical connector 426 substantially automatically aligns with the corresponding electrical connector 20 of the ventilator. It will, however, be appreciated that any known or suitable alternative number and/or configuration of electrical connector(s) could be employed, without departing from the scope of the invention. It will also be appreciated that although batteries 424 (FIG. 14) of detachable battery pack 412 and internal rechargeable battery 410 (FIG. 12) are contemplated as being lithium ion batteries, any known or suitable alternative number, configuration and/or type of batteries could be employed.

Enclosure 414 further includes at least one fastening mechanism, which in the example shown and described herein includes first and second protrusions 428 and 430 extending outwardly from first and second ends 416 and 418, respectively, of battery pack enclosure 414. As shown in FIG. 14, protrusions 428 and 430 are structured to engage corresponding recesses 22 and 24 at opposing ends 14 and 16, respectively, of cavity 12 in ventilator housing 4, in order to removably couple enclosure 414 to the housing. More specifically, when detachable battery back 412 is inserted into cavity 12 in the appropriate orientation, first protrusion 428 engages the corresponding recess 22 at first end 14 of cavity 12. Detachable battery pack 412 is then pivoted (e.g., counterclockwise with respect to FIG. 14) until second protrusion 430 engages recess 24 at second end 16 of cavity 12. In this manner, detachable battery pack 412 snaps into the desired predetermined orientation, and is secured within cavity 12 of ventilator housing 4.

In an exemplary embodiment, detachable battery pack 412 further includes a release mechanism 432 (FIGS. 2, 3 and 14) disposed on second side 422 of battery pack enclosure 414 so that it is accessible from exterior 8 of ventilator housing 4. As best shown in the sectional view of FIG. 14, at least one of the aforementioned first and second protrusions 428 and 430 is movably coupled to release mechanism 432 in order that movement of the release mechanism results in a corresponding movement of such protrusion(s) 428 and/or 430 to disengage a corresponding recess 22 and 24 of cavity 12 of ventilator housing 4, and release detachable battery pack 412 to be removed therefrom.

Continuing to refer to FIG. 14, it will be appreciated that cavity 12 of housing 4 of ventilator 2 has a first shape, and that first side 420 of detachable battery pack enclosure 414 has a corresponding second shape. Thus, when detachable battery pack 412 is inserted into cavity 12 in the predetermined orientation, as shown in FIG. 14, the second shape of battery enclosure 414 corresponds with the first shape of cavity 12 of ventilator housing 4, in order that detachable battery pack 412 is nested within the cavity. In the example of FIG. 14, which is not meant to limit the scope of the invention in any way, the second end of cavity 12 of ventilator housing 4 has an arcuate portion 18, and second end 418 of detachable battery pack enclosure 414 has a corresponding arcuate portion 419. The corresponding arcuate portions 18 and 419 facilitate insertion of battery pack 412 into cavity 12 in the appropriate orientation. In fact, it is substantially impossible for detachable battery pack 412 to be incorrectly inserted into cavity 12 in any other orientation. This advantageously eliminates the possibility of the patient or caretaker incorrectly attaching detachable battery pack 412 resulting, for example, in the ventilator not receiving power from detachable battery pack 412.

As shown in FIG. 13, the present invention contemplates providing detachable battery pack 412 with a charge indicator 434 structured to indicate the measured capacity of the number of batteries 424 (FIG. 14) disposed within enclosure 414. As employed herein, the term "measured capacity" refers to the remaining power of battery pack 412 as compared, for example, to a fully charged battery pack, which would be at its maximum capacity. Charge indicator 434 in the example of FIG. 13 includes a plurality of light emitting diodes (LEDs) 435, which are electrically connected to batteries 424 (FIG. 14) of detachable battery pack 412. LEDs 435 are arranged in a line, with charge indicator 434 being designed to illuminate a number of LEDs 435 (i.e., a portion of the line), which is indicative of the measured capacity of detachable battery pack 412.

It will be appreciated that any known or suitable alternative type of change indicator other than LEDs 435 could be employed in any suitable number and/or configuration, without departing from the scope of the invention. It will also be appreciated that, although the indication (e.g., illumination of the number of LEDs) could be provided in any known or suitable manner (e.g., without limitation, automatically), charge indicator 434 of FIG. 13 includes a resilient tab 436, which is depressible to complete a circuit (not expressly shown) between batteries 424 (FIG. 14) and LEDs 435, in order to "test" battery pack 412 (i.e., illuminate the corresponding number of LEDs 435).

It will further be appreciated that the detachable battery pack 412 may include any known or suitable additional indicia. For example, in the non-limiting embodiment illustratively shown in FIG. 13, battery pack 412 includes indicators 437 and 438 which may comprise, for example and without limitation, a charging light (e.g., LED) 437, which could be adapted to blink while detachable battery pack 412 is charging, and another light (e.g., LED) 438, which could be adapted to illuminate when a predetermined threshold capacity (e.g., a minimum acceptable capacity before requiring replacement or transfer to another power source; maximum capacity) of the detachable battery pack is reached.

Figure 15:
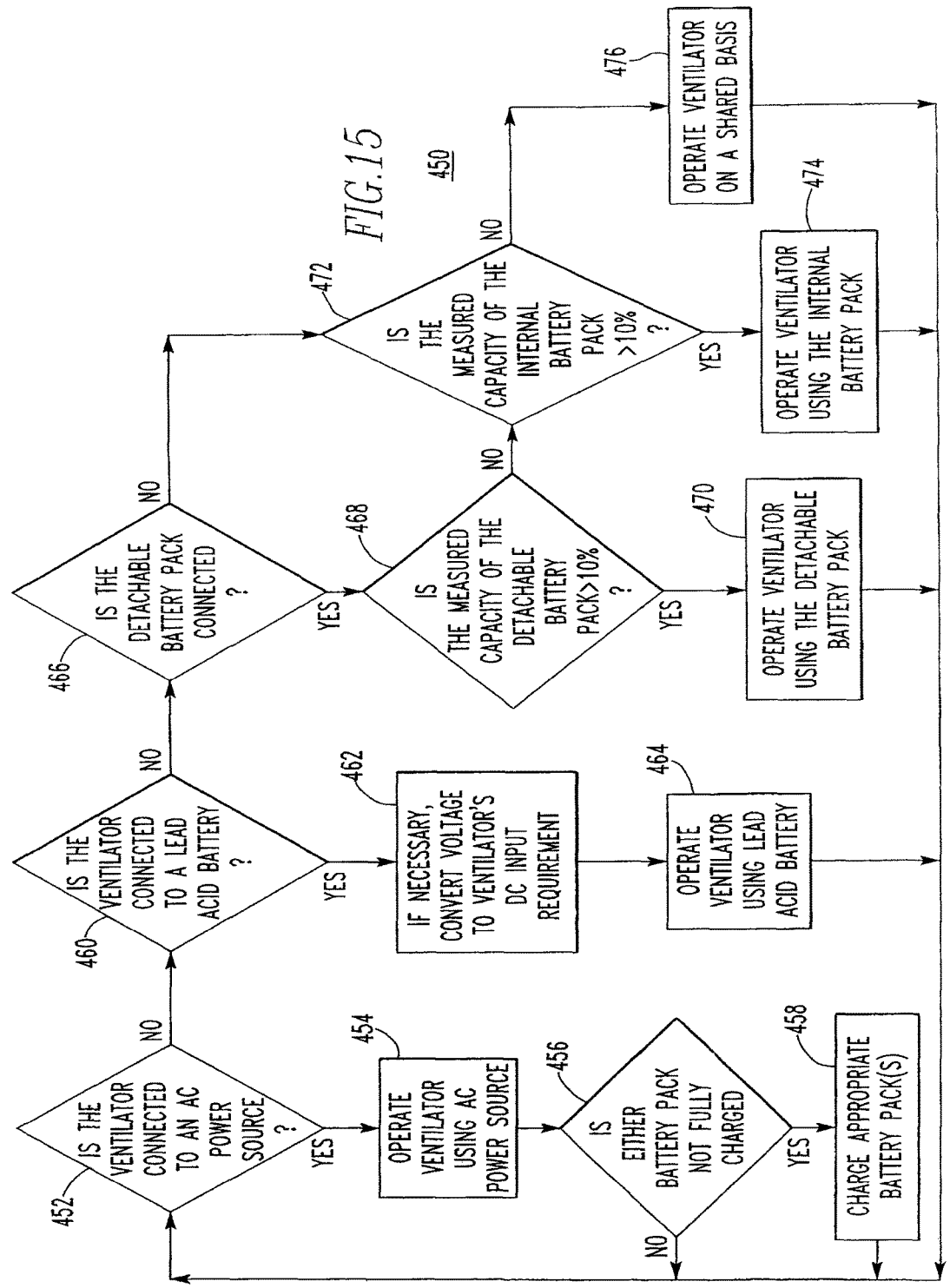
FIG. 15 is a flow diagram for a method of supplying power to a medical ventilator.

FIG. 15 shows a method 450 of operating ventilator 2 in accordance with the predetermined hierarchy of the four aforementioned sources of power 402, 406, 410, and 412 (FIG. 12), in accordance with an embodiment of the invention. Specifically, at a first step 452, a determination is made as to whether or not the first power connection (e.g., AC power connector 404 of FIG. 12) is electrically connected to the AC power source 402. If so, power control mechanism 26 (shown in simplified form in FIG. 12) causes power to be supplied to ventilator 2 from the AC power source 402. As the ventilator is operated using the AC power source 402, a determination is made, at step 456, whether or not either of the internal rechargeable battery pack 410 or the detachable battery pack 412 (FIGS. 2, 3, 10 and 12-14) is fully charged. If not, then charger 28 charges the appropriate battery pack(s) 410 and/or 412, at step 458. If both battery packs 410 and 412 are already fully charged, or after they have been fully charged at step 458, the method repeats, starting over again at step 452, with the step of determining whether or not AC power connector 404 is electrically connected to the AC power source 402.

If, at step 452, it is determined that AC power connector 404 of the ventilator 2 is not electrically connected to AC power source 402, then the method moves to step 460 where a determination is made as to whether or not the second power connection (e.g., lead acid battery connector 408 of FIG. 12) is electrically connected to the lead acid battery 406. If so, the method continues to step 462, which is optional. Specifically, at step 462, if necessary, the voltage from the lead acid battery 406 is converted to the appropriate direct current (DC) requirement of ventilator 2. Then, at step 464, power control mechanism 26 causes power to be supplied to the ventilator from the lead acid battery 406. Meantime, power control mechanism 26 continues to evaluate whether or not ventilator 2 and, in particular, AC power connector 404, has been connected to AC power source 402. This is true at all times during the operation of ventilator 2. In other words, there is a predetermined hierarchy of the four sources of power 402, 406, 410, and 412 (all shown in FIG. 12), wherein AC power source 402 preferably takes priority, followed by lead acid battery 406, then detachable battery pack 412, and finally internal rechargeable battery pack 410.

Continuing to refer to method 450 in accordance with the example of FIG. 15, if at step 460, it is determined that lead acid battery connector 408 of the ventilator 2 is not connected to the lead acid battery 406, then a determination is made, at step 466, as to whether or not the detachable battery pack 412 is electrically connected to ventilator 2. If the answer to that inquiry is yes, then at step 468, the measured capacity of the detachable battery pack 412 is evaluated and, if it exceeds a predetermined threshold (e.g., without limitation, greater than 10 percent of the maximum capacity of the detachable battery pack 412), then the method moves to step 470. At step 470, power is supplied to the ventilator using the detachable battery pack 412. If, however, at step 466, it is determined that the detachable battery pack 412 is not electrically connected to the ventilator, or at step 468 it is determined that the measured capacity of the detachable battery pack 412 is less than the predetermined threshold, then the method proceeds to step 472.

At step 472, the measured capacity of the internal rechargeable battery pack 410 is evaluated and, if it exceeds a predetermined threshold (e.g., without limitation, greater than 10 percent of the maximum capacity of the internal rechargeable battery pack 410), then the method moves to step 474. Alternatively, if the measured capacity of the internal rechargeable battery pack 410 is not greater than the predetermined threshold, then the method moves to step 476. At step 474, power is supplied to ventilator 2 to operate the ventilator using the internal rechargeable battery pack 410, whereas at step 476, power is supplied to the ventilator from both detachable battery pack 412 and internal rechargeable battery pack 410, on a predetermined shared basis.

More specifically, step 476 generally occurs when both internal rechargeable battery pack 410 and detachable battery pack 412 have a measured capacity of less than 10 percent of their respective maximum capacities. Under such circumstances, the supply of power to the ventilator will be shared by the two battery packs 410 and 412 according to the rule that the battery pack with the greater capacity shall provide the greater electrical current, such that both battery packs 410 and 412 shall reach zero percent capacity substantially simultaneously. In accordance with one non-limiting example, internal rechargeable battery pack 410 and detachable battery pack 412 together provide sufficient power for ventilator 2 to operate under normal operating conditions, for at least four hours. It will, however, be appreciated that battery packs having durations of less than or greater than four hours, are also within the scope of the invention.

It will, therefore, be appreciated that, in accordance with the disclosed method 450, the electrical connection or disconnection of any of the four sources of power 402, 406, 410, and 412 will not result in any interruption of power to the ventilator 2, provided that at least one of the sources of power 402, 406, 410, and 412 remains electrically connected, and is within a predetermined specification (e.g., without limitation, measured capacity). It will also be appreciated that detachable battery pack 412 provides a relatively lightweight mechanism for supplying power to the ventilator 2, substantially indefinitely. For example, a plurality of detachable battery packs 412 (only one is shown) could be employed wherein, when one of the detachable battery packs is electrically connected to the ventilator, the others are being charged using any known or suitable charger or battery recharging device (not shown). When detachable battery pack 412, which is electrically connected to the ventilator, is discharged to the predetermined threshold capacity, it can be quickly and easily replaced with one of the charged replacement detachable battery packs. During the exchange of the detachable battery packs (i.e., replacing a discharged battery pack with a charged one), the internal battery pack 410 will provide the necessary power to ventilator, to avoid any unintended interruption in power.

Accordingly, ventilator 2 of the present invention provides a compact and rugged unit which, with its modular design, is portable to facilitate patient mobility so as to maintain the lifestyle of the patient as much as possible. Thus, in accordance with the invention, one single portable ventilator 2 is capable of being operated in a variety of modes to provide a plurality of different ventilation therapies to the patient. Among other benefits and advantages, the ventilator also includes a user-friendly user interface 300, is capable of recording, transferring, and reporting clinical data, is selectively connectable to a variety of accessories (e.g., without limitation, a humidifier; an oxygen mixer; a pulse oximeter; a carbon dioxide monitor) and devices (e.g., without limitation, the Internet; a printer; a computer). The ventilator also has a number of convenient and cost-effective features such as, for example and without imitation, a porting system 100 for quickly and easily configuring the ventilator for operation in the desired mode, detachable battery pack 412 and four sources of power, and a modular inlet airflow assembly 200, which can be selectively removed from the ventilator 2 to service (e.g., sterilize) the remainder of ventilator, without requiring substantial disassembly or replacement of the ventilator.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A detachable battery pack for a ventilator, the ventilator including a housing having an exterior surface and a cavity having a first shaped surface interior to the housing and extending inwardly from the exterior surface, the detachable battery pack comprising:
   an enclosure structured to be inserted into the cavity, the enclosure including a first end, a second end disposed opposite and distal from the first end, a first side, and a second side;
   a number of batteries enclosed by the enclosure;
   an electrical connector electrically connected to the number of batteries, the electrical connector being structured to electrically connect the detachable battery pack to the ventilator in order to provide power to the ventilator; and
   at least one fastening mechanism structured to removably couple the enclosure to the housing, wherein the cavity, the enclosure, or both are configured such that the detachable battery pack will only fit within the cavity in one predetermined orientation,
   wherein the enclosure has a second shaped surface that cooperates with the first shaped surface of the cavity to facilitate insertion of the enclosure within the cavity in only the one predetermined orientation,
   wherein the first shaped surface of the cavity and the second shaped surface of the enclosure are configured to allow a pivoting movement relative to each other about the first end of the enclosure to removably couple the enclosure within the cavity of the housing.

2. The detachable battery pack of claim 1, wherein the cavity of the housing of the ventilator has the first shaped surface, wherein the first side of the enclosure of the detachable battery pack has the second shaped surface, and wherein, when the detachable battery pack is inserted into the cavity in the predetermined orientation, the second shaped surface of the enclosure is structured to correspond with the first shaped surface of the housing, in order that the detachable battery pack is nested within the cavity.

3. The detachable battery pack of claim 1, wherein the cavity of the housing of the ventilator includes a first end, a second end disposed opposite and distal from the first end of the cavity, and the first shaped surface comprises an arcuate shaped surface, wherein the arcuate shaped surface of the cavity is disposed at or about the second end of the cavity, wherein the first side of the enclosure includes the second shaped surface comprising an arcuate shaped surface disposed at or about the second end of the enclosure, and wherein the arcuate shaped surface of the enclosure corresponds to the arcuate shaped surface of the cavity in order to facilitate insertion and pivoting of the battery pack into the cavity in the predetermined orientation.

4. The detachable battery pack of claim 3, wherein the arcuate shaped surface of the cavity is provided on a surface interior to the housing at the second end of the cavity and the arcuate shaped surface of the enclosure is provided on an external surface of the enclosure at the second end.

5. The detachable battery pack of claim 3, wherein the arcuate shaped surface is substantially concealed by the cavity upon insertion.

6. The detachable battery pack of claim 1, wherein the cavity of the housing of the ventilator has a first end and a second end disposed opposite and distal from the first end of the cavity, wherein the at least one fastening mechanism comprises a first protrusion extending outwardly from the enclosure of the detachable battery pack at or about the first end of the enclosure, and a second protrusion extending outwardly from the enclosure of the detachable battery pack at or about the second end of the enclosure, and wherein, when the detachable battery pack is inserted into the cavity in the appropriate orientation, the first protrusion is structured to engage the housing at or about the first end of the cavity, and the second protrusion is structured to engage the housing at or about the second end of the cavity, in order that the detachable battery pack snaps into the predetermined orientation and is secured within the cavity.

7. The detachable battery pack of claim 6, wherein the at least one fastening mechanism further comprises a release mechanism disposed on the second side of the enclosure of the detachable battery pack, and wherein at least one of the first protrusion and the second protrusion is movably coupled to the release mechanism, in order that movement of the release mechanism results in a corresponding movement of the at least one of the first protrusion and the second protrusion, thereby disengaging the detachable battery pack from the housing of the ventilator.

8. The detachable battery pack of claim 1, wherein, when the enclosure is disposed in the predetermined orientation within the cavity, the second side of the enclosure is structured to be substantially flush with respect to the exterior surface of the housing adjacent the cavity.

9. The detachable battery pack of claim 1, wherein the enclosure further include a charge indicator structured to indicate the measured capacity of the number of batteries.

10. The detachable battery pack of claim 9, wherein the charge indicator comprises a plurality of LEDs electrically connected to the number of batteries, and wherein the number of batteries illuminate a number of the LEDs corresponding to the measured capacity of the number of batteries of the detachable battery pack.

11. The detachable battery pack of claim 1, wherein the ventilator further includes an electrical connector disposed within the cavity of the housing, wherein the electrical connector of the detachable battery pack is disposed on the first side of the enclosure of the detachable battery pack, and wherein, when the detachable battery pack is inserted into the cavity in the predetermined orientation, the electrical connector of the detachable battery pack is structured to align with and electrically connect to the electrical connector of the ventilator.

12. The detachable battery pack of claim 1, wherein surfaces of the first end, the second end, the first side, a left side, and a right side of the enclosure are substantially concealed by the cavity, and a surface of the second side is exposed.

13. A ventilator comprising:
(a) a housing having an exterior surface and a cavity having a first shaped surface interior to the housing and extending inwardly from the exterior surface; and
(b) a detachable battery pack comprising:
(1) an enclosure structured to be inserted into the cavity, the enclosure including a first end, a second end disposed opposite and distal from the first end, a first side, and a second side;
(2) a number of batteries enclosed by the enclosure;
(3) an electrical connector electrically connected to the number of batteries, the electrical connector being structured to electrically connect the detachable battery pack to the ventilator in order to provide power to the ventilator; and
(4) at least one fastening mechanism structured to removably couple the enclosure to the housing, wherein the cavity, the enclosure, or both are configured such that the detachable battery pack will only fit within the cavity in one predetermined orientation, wherein the enclosure has a second shaped surface that cooperates with the first shaped surface of the cavity to facilitate insertion of the enclosure within the cavity in only the one predetermined orientation,
wherein the first shaped surface of the cavity and the second shaped surface of the enclosure are configured to allow a pivoting movement relative to each other about the first end of the enclosure to removably couple the enclosure within the cavity of the housing.

14. The ventilator of claim 13, wherein the cavity of the housing of the ventilator includes a first end, a second end disposed opposite and distal from the first end of the cavity, and the first shaped surface being an arcuate shaped surface, wherein the arcuate shaped surface of the cavity is disposed at or about the second end of the cavity, wherein the first side of the enclosure includes the second shaped surface, the second shaped surface being an arcuate shaped surface disposed at or about the second end of the enclosure, and wherein the arcuate shaped surface of the enclosure corresponds to the arcuate shaped surface of the cavity in order to facilitate insertion and pivoting of the battery pack into the cavity in the predetermined orientation.

15. The ventilator of claim 13, wherein the cavity of the housing of the ventilator has a first end and a second end disposed opposite and distal from the first end of the cavity, wherein the at least one fastening mechanism of the detachable battery pack comprises a first protrusion extending outwardly from the enclosure of the detachable battery pack at or about the first end of the enclosure, and a second protrusion extending outwardly from the enclosure of the detachable battery pack at or about the second end of the enclosure, and wherein, when the detachable battery pack is inserted into the cavity of the housing of the ventilator in the appropriate orientation, the first protrusion engages the housing of the ventilator at or about the first end of the cavity, and the second protrusion engages the housing of the ventilator at or about the second end of the cavity, in order that the detachable battery pack snaps into the predetermined orientation and is secured within the cavity.

16. The ventilator of claim 15, wherein the at least one fastening mechanism of the detachable battery pack further comprises a release mechanism disposed on the second side of the enclosure of the detachable battery pack, and wherein at least one of the first protrusion and the second protrusion is movably coupled to the release mechanism, in order that movement of the release mechanism results in a corresponding movement of the at least one of the first protrusion and the second protrusion, thereby disengaging the detachable battery pack from the housing of the ventilator.

17. The ventilator of claim 13, wherein, when the enclosure of the detachable battery pack is disposed in the predetermined orientation within the cavity of the housing of the ventilator, the second side of the enclosure is substantially flush with respect to the exterior surface of the housing adjacent the cavity.

18. The ventilator of claim 13, wherein the housing of the ventilator further includes an electrical connector disposed within the cavity, wherein the electrical connector of the detachable battery pack is disposed on the first side of the enclosure of the detachable battery pack, and wherein, when the detachable battery pack is inserted into the cavity of the housing of the ventilator in the predetermined orientation, the electrical connector of the detachable battery pack aligns with and electrically connects to the electrical connector of the ventilator.

19. The ventilator of claim 13, wherein surfaces of the first end, the second end, the first side, a left side, and a right side of the enclosure are substantially concealed by the cavity, and a surface of the second side is exposed.

* * * * *